(12) United States Patent
    Couturier

(10) Patent No.: US 9,638,642 B2
(45) Date of Patent: May 2, 2017

(54) APPARATUS AND METHOD FOR OPTICALLY SCANNING A SURFACE OF AN OBJECT UNDER ADVERSE EXTERNAL CONDITION

(71) Applicant: CENTRE DE RECHERCHE INDUSTRIELLE DU QUEBEC, Quebec (CA)

(72) Inventor: Jean-Pierre Couturier, Quebec (CA)

(73) Assignee: CENTRE DE RECHERCE INDUSTRIELLE DU QUEBEC, Quebec (CA)

( * ) Notice: Subject to any disclaimer, the term of this patent is extended or adjusted under 35 U.S.C. 154(b) by 133 days.

(21) Appl. No.: 14/555,878

(22) Filed: Nov. 28, 2014

(65) Prior Publication Data

US 2016/0153917 A1    Jun. 2, 2016

(51) Int. Cl.
    *G06K 9/40*       (2006.01)
    *G01N 21/898*     (2006.01)
    *G01N 21/88*      (2006.01)

(52) U.S. Cl.
    CPC ..... *G01N 21/8986* (2013.01); *G01N 21/8851* (2013.01); *G01N 2201/0612* (2013.01)

(58) Field of Classification Search
    CPC ........... G01N 21/8986; G01N 21/8851; G01N 2021/8896; G01N 2201/0612; G01N 2021/8466
    USPC ................................ 382/100, 141, 152, 274
    See application file for complete search history.

(56) References Cited

U.S. PATENT DOCUMENTS

| | | | |
|---|---|---|---|
| 5,960,104 A | 9/1999 | Conners et al. | |
| 6,122,065 A | 9/2000 | Gauthier | |
| 7,424,170 B2 | 9/2008 | Steinberg et al. | |
| 7,429,999 B2 | 9/2008 | Poulin et al. | |
| 7,539,342 B2 | 5/2009 | Tabata et al. | |
| 8,193,481 B2 | 6/2012 | Garneau et al. | |
| 8,682,097 B2 | 3/2014 | Steinberg et al. | |
| 8,708,582 B2 | 4/2014 | Gagnon et al. | |
| 8,723,945 B2 | 5/2014 | Lessard | |
| 2012/0218437 A1* | 8/2012 | Hermary | G01B 11/245 348/222.1 |
| 2013/0208995 A1* | 8/2013 | Zamfir | H04N 5/217 382/275 |
| 2014/0307119 A1 | 10/2014 | Gagnon et al. | |

* cited by examiner

*Primary Examiner* — Andrew Moyer
(74) *Attorney, Agent, or Firm* — Jean-Claude Boudreau

(57) ABSTRACT

An apparatus and a method for optically scanning a surface of an object under an adverse external condition to which optical components are subjected, such as cameras and lighting sources sensitive to soiling, make use of a first imaging sensor unit having its optical components subjected to the adverse external condition, and being configured for generating reflection intensity image data associated with a target surface. A second imaging sensor unit having its optical components substantially not subjected to the adverse external condition, is configured for generating reflection intensity image data associated with a reference surface. Correction data are calculated from a comparison between the reflected intensity image data associated with the target and reference surfaces, which correction data are then applied to the reflected intensity image data associated with the target surface to generate corrected intensity image data compensating for the adverse external condition.

21 Claims, 12 Drawing Sheets

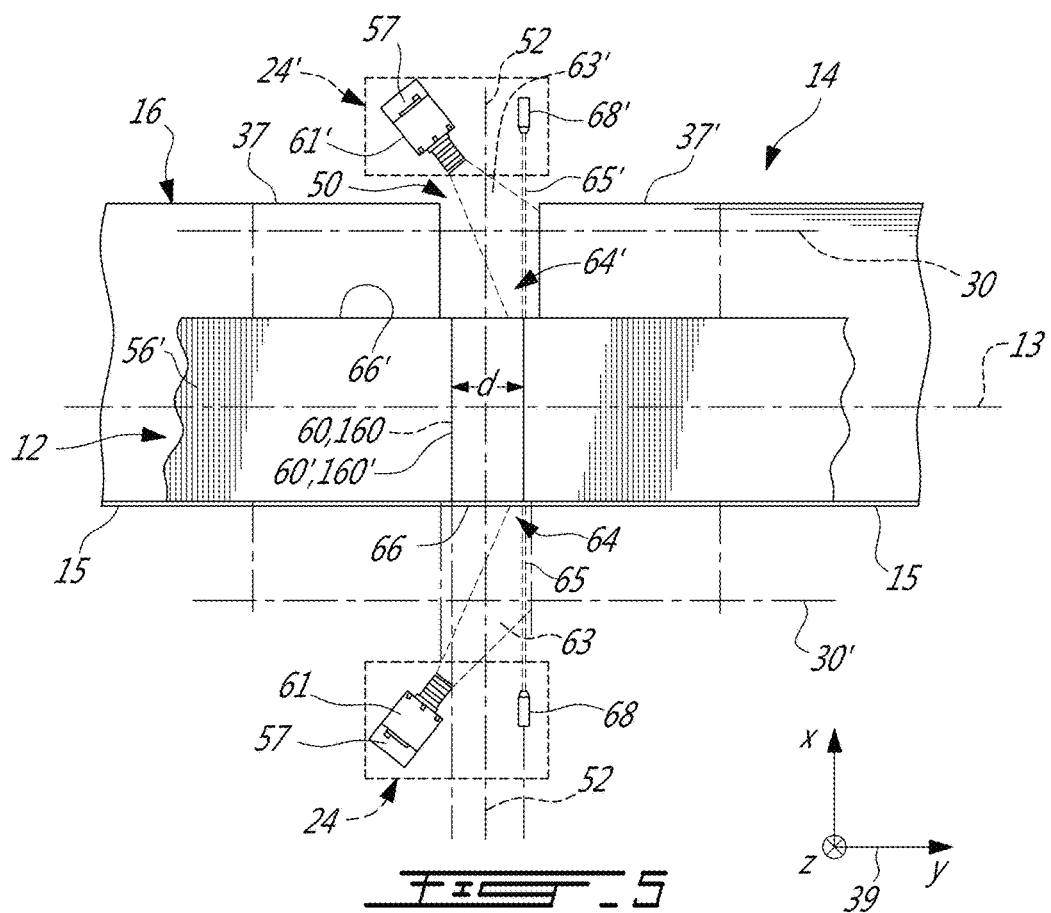
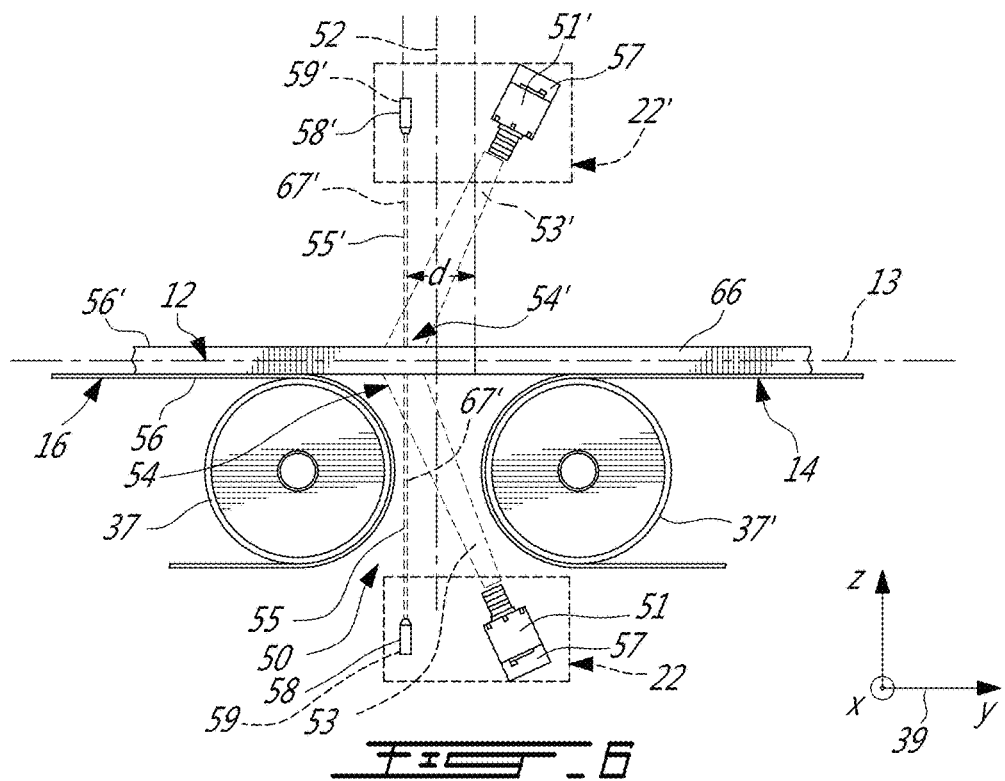

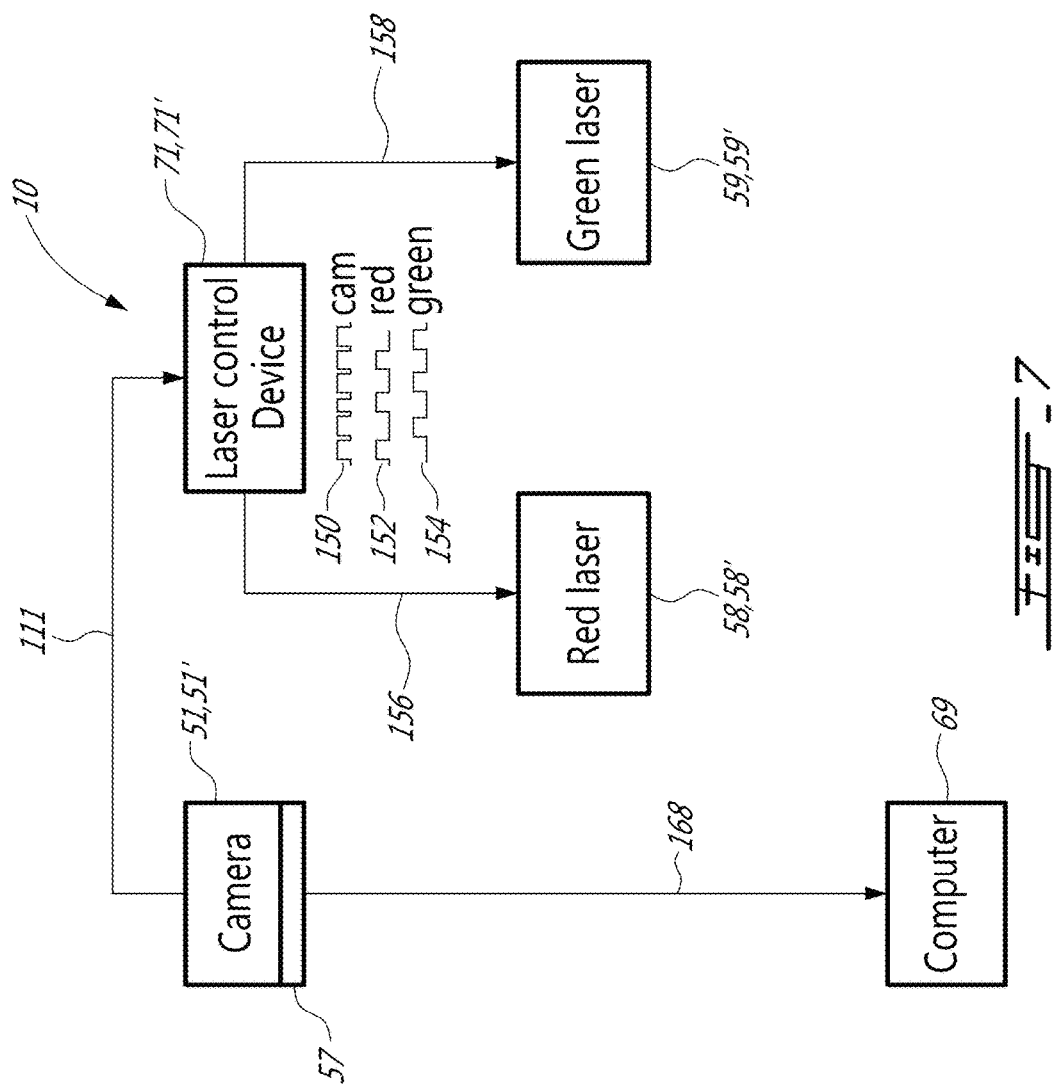

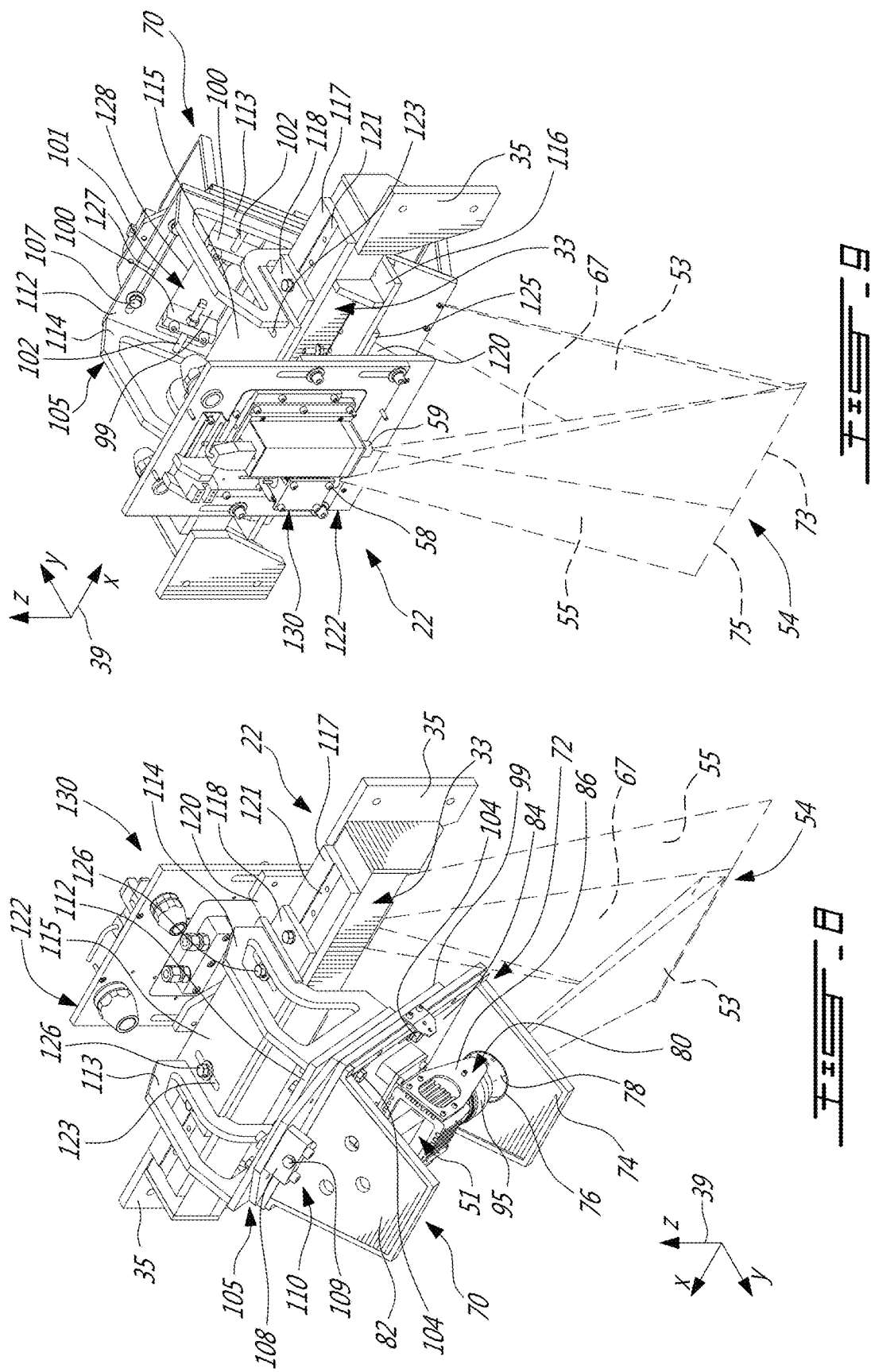

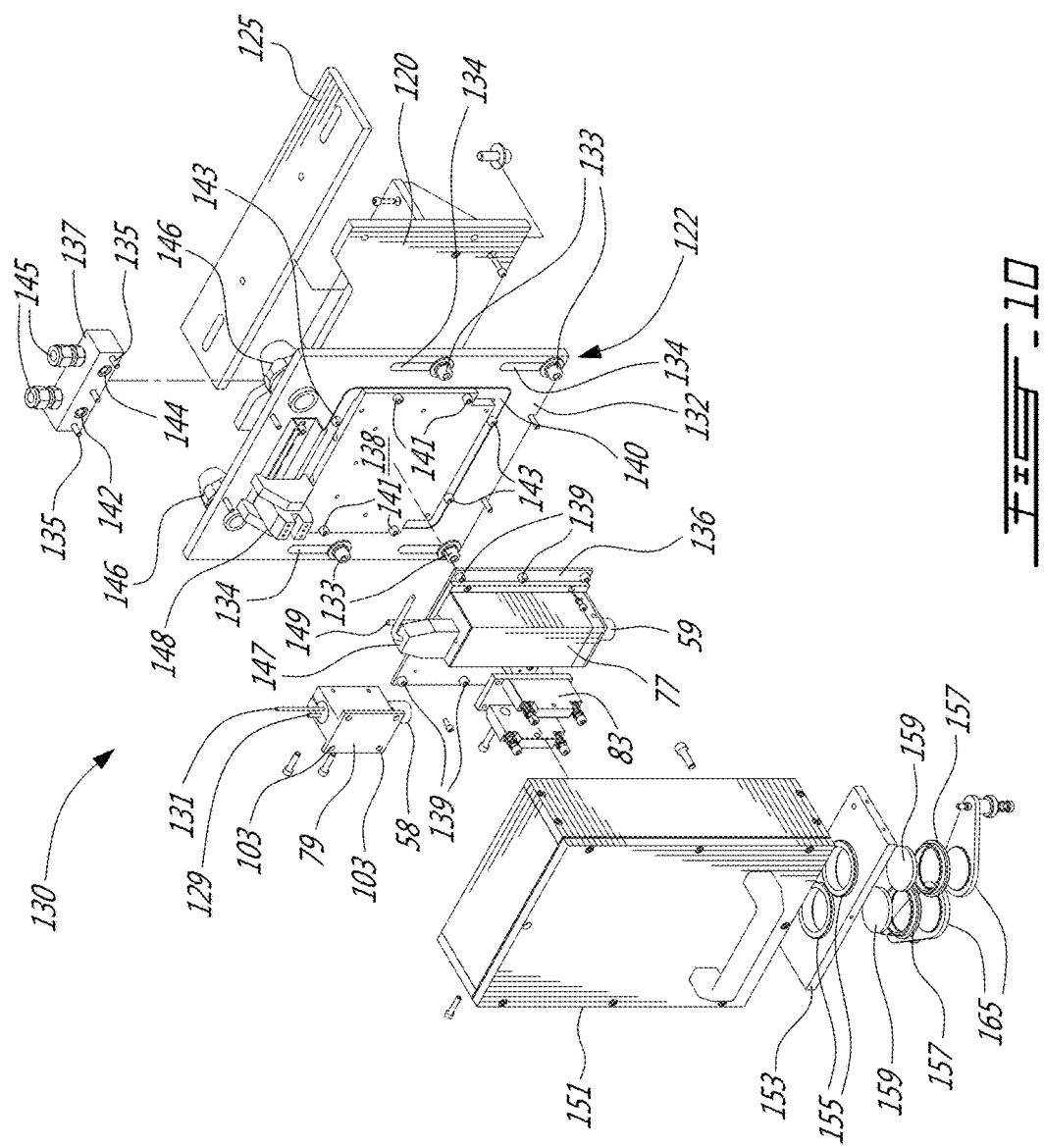

FIG. 12c
FIG. 12d
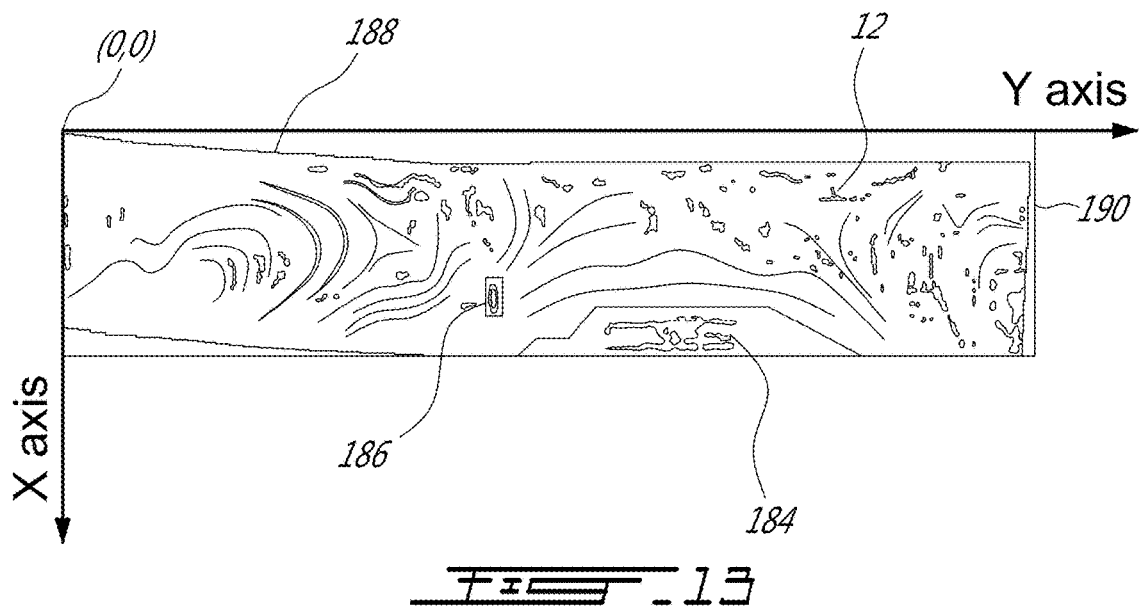
FIG. 13

Luminance (sapwood) = 100

Luminance (sapwood) = 75

Luminance (sapwood) = 100

APPARATUS AND METHOD FOR OPTICALLY SCANNING A SURFACE OF AN OBJECT UNDER ADVERSE EXTERNAL CONDITION

TECHNICAL FIELD

The present invention pertains to the field of image data processing. More particularly, the invention refers to apparatus and methods for optically scanning the surface of an object, e.g. for grading, sorting or quality control purposes in product manufacturing industries, under external soiling condition.

BACKGROUND OF THE INVENTION

During the past years, systems for scanning the surface of moving objects have been developed and applied for grading, sorting or quality control purposes in many high volume manufacturing applications such as found in the automotive, consumer electronics, agricultural, food or wood and lumber processing industries. Such scanning systems typically use digital cameras generating 2D images from which reflection-related characteristics of the surface of objects under inspection are detected, which cameras can also be used as profile sensors based on laser triangulation to measure geometrical and other 3D surface characteristics of the inspected objects. In some applications, many characteristics of the object surface must be detected, thus requiring integration of several optical scanning sensors using associated lighting devices and whose outputs are combined for the desired purpose. A known defect detection system for lumber using that approach is disclosed in U.S. Pat. No. 5,960,104 to Conners et al., wherein color cameras are employed to detect surface features (2D), and a laser profiling device is employed to perform three-dimensional (3D) shape detection. In some prior known scanning apparatus, each scanning unit includes a digital camera associated with a single laser directing a linear-shaped laser beam onto the board surface under inspection, to form a laser line that intersects the field of view of the camera, which is capable of generating a 3D profile image of the board surface through a laser triangulation technique based on detected position of the laser line. Furthermore, to provide scanning unit compactness, it is known that from the same imaging sensors (CMOS or CCD) provided on such 3D digital camera, it is possible to simultaneously generate a 2D image of the same board surface from the measured mean intensities of the reflected laser line, such mode of operation being used by the optical inspection apparatus disclosed in U.S. Pat. No. 8,723,945 to Lessard. Moreover, a linear laser source can also be used to provide lighting in cases where only 2D imaging is required.

Typically, as shown in FIG. 1, a 2D image can be expressed in terms of a plurality of line image vectors forming a matrix with reference to orthogonal first and second axis X and Y, such as obtained while moving the inspected object (or the camera) relative to the camera (or the object) along Y axis, while performing laser scanning using a linear laser source that extends along X axis. Ideally, the intensity value of each image pixel should indicate the reflection-related characteristics (preferably referred to as luminance, but could be also referred to as reflectance, brightness or lightness) of the corresponding area of the scanned surface. However in practice, the measured variation may be affected by adverse external conditions to which the optical components of the sensor units (cameras, lighting sources) are subjected. In typical industrial environments, these optical components may be exposed at various levels to soiling caused by dirt and dust which deposit with time on the outer surface of optical light transmission parts such as protecting glass for camera objective and laser source, which soiling acts as an optical mask affecting intensity of light transmitted therethrough. Depending on the level and location of soiling, the intensity of light directed to the inspected surface (i.e. soiling affecting the lighting) or the intensity of reflected light reaching the imaging sensor (i.e. soiling affecting the image sensing) will be affected, providing an optical measurement which is more of less representative of the actual reflection-related characteristics of the inspected surface. Hence, there is a need for a method aimed at correcting reflection light intensity of a digital image to compensate for adverse external conditions to which the optical components of the sensor units are subjected.

SUMMARY OF THE INVENTION

It is a main object of the present invention to provide apparatus and methods for optically scanning a surface of an object under an external soiling condition.

According to the above-mentioned main object, from a broad aspect of the present invention, there is provided an apparatus for optically scanning a surface of an object under an external soiling condition, comprising a first imaging sensor unit having one or more optical components subjected to the external soiling condition, a sensing field defining a scanning zone intersecting a target surface of the object, and being configured for generating reflection intensity image data associated with the target surface. The apparatus further comprises a second imaging sensor unit having one or more optical components substantially not subjected to the external soiling condition, a sensing field defining a scanning zone intersecting a reference surface of the object and being configured for generating reflection intensity image data associated with the reference surface. The apparatus further comprises data processing means programmed to calculate correction data from a comparison between the reflected intensity image data associated with the target and reference surfaces, and further programmed to apply the correction data to the reflected intensity image data associated with the target surface to generate corrected intensity image data compensating for the external soiling condition.

According to the same main object, from another broad aspect, there is provided an apparatus for optically scanning a surface of at least one of a plurality of objects being serially transported under an external soiling condition, comprising a first imaging sensor unit having one or more optical components subjected to the external soiling condition, a sensing field defining a scanning zone intersecting a target surface of the object and being configured for generating reflection intensity image data associated with the target surface. The apparatus further comprises a second imaging sensor unit having one or more optical components substantially not subjected to the external soiling condition, a sensing field defining a scanning zone intersecting a reference surface of the object and configured for generating reflection intensity image data associated with the reference surface. The apparatus further comprises data processing means programmed to calculate correction data from a comparison between the reflected intensity image data associated with the target and reference surfaces, and further programmed to apply the correction data to the reflected intensity image data associated with the target surface to generate corrected intensity image data compensating for the external soiling condition.

According to the same main object, from a further broad aspect, there is provided a method for optically scanning a surface of an object under external soiling condition, for use with a first imaging sensor unit having one or more optical components subjected to the external soiling condition, a sensing field defining a scanning zone intersecting a target surface of the object and configured for generating reflection intensity image data associated with the target surface, comprising the steps of: i) providing a second imaging sensor unit having one or more optical components substantially not subjected to the external soiling condition, a sensing field defining a scanning zone intersecting a reference surface of the object, and being configured for generating reflection intensity image data associated with the reference surface; ii) calculating correction data from a comparison between the reflected intensity image data associated with the target and reference surfaces; and iii) applying the correction data to the reflected intensity image data associated with the target surface to generate corrected intensity image data compensating for the external soiling condition.

According to the same main object, from a further broad aspect, there is provided a method for optically scanning a surface of at least one of a plurality of objects being serially transported under external soiling condition, for use with a first imaging sensor unit having one or more optical components subjected to the external soiling condition, a sensing field defining a scanning zone intersecting a target surface, and being configured for generating reflection intensity image data associated with the target surface, comprising the steps of: i) providing a second imaging sensor unit having one or more optical components substantially not subjected to the external soiling condition, a sensing field defining a scanning zone intersecting a reference surface of the object, and being configured for generating reflection intensity image data associated with the reference surface; ii) calculating correction data from a comparison between the reflected intensity image data associated with the target and reference surfaces; and iii) applying the correction data to the reflected intensity image data associated with the target surface to generate corrected intensity image data compensating for the external soiling condition.

The above summary of invention has outlined rather broadly the features of the present invention. Additional features and advantages of some embodiments illustrating the subject of the claims will be described hereinafter. Those skilled in the art will appreciate that they may readily use the description of the specific embodiments disclosed as a basis for modifying them or designing other equivalent structures or steps for carrying out the same purposes of the present invention. Those skilled in the art will also appreciate that such equivalent structures or steps do not depart from the scope of the present invention in its broadest form.

BRIEF DESCRIPTION OF THE DRAWINGS

Some embodiments of the present invention will now be described in detail with reference to the accompanying drawings in which:

FIG. 5 is a schematic sectional view of the apparatus along section lines 5-5 of FIG. 3, illustrating the configuration of optical elements used for scanning the object side surfaces;

FIG. 6 is a schematic sectional view of the apparatus along section lines 6-6 of FIG. 3, illustrating the configuration of optical elements used for scanning the object top and bottom surfaces;

FIG. 7 is a schematic block diagram of the scanning apparatus showing its basic components;

FIG. 8 is a perspective front view of an imaging sensor unit provided on the apparatus of FIG. 2, showing the digital camera;

FIG. 9 is a perspective rear view of the imaging sensor unit of FIG. 8, showing the laser assembly without its enclosure;

FIG. 10 is an exploded view of the laser assembly of FIG. 8, provided with its enclosure;

FIGS. 12c and 12d are realigned image representations of top and bottom surfaces of the wooden board of FIG. 12;

FIG. 13 is an example of an analysed image showing classified characteristic areas delimited by polygons;

Figure 1:
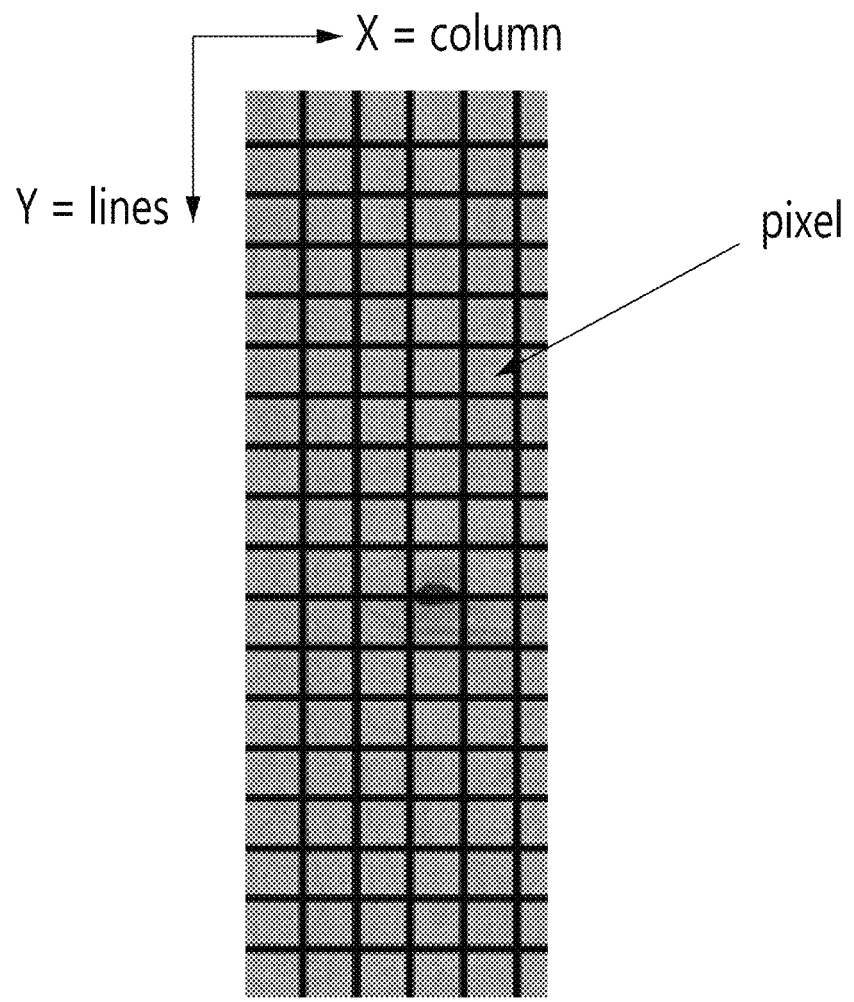
FIG. 1 is a schematic representation of a 2D image expressed in terms of a plurality of line image vectors forming a matrix (prior art)

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

DETAILED DESCRIPTION

While the invention has been illustrated and described in detail below in connection with example embodiments, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

The apparatus and method for optically scanning a surface of an object under an adverse external according to example embodiments of the present invention, will now be described in the context of optical surface inspection of wooden boards, wherein the reflection-related characteristics of the scanned surface are associated with detected knots, mineral streaks, slits, heartwood and sapwood areas. However, it is to be understood that the proposed optical scanning apparatus and method according to the invention are not limited to wooden product inspection, and can be adapted to other inspection applications such as found in the automotive, consumer electronics, agricultural, and food processing industries. Furthermore, although the intensity value of each image pixel that indicates the reflection-related characteristics is hereinabove referred to as luminance, it could be also referred to as reflectance, brightness or lightness of the corresponding area of the scanned surface. Moreover, the intensity of another component of an image signal (e.g. RGB, LAB, HSL, etc.) may also be corrected according to the proposed apparatus and method.

Figure 2:
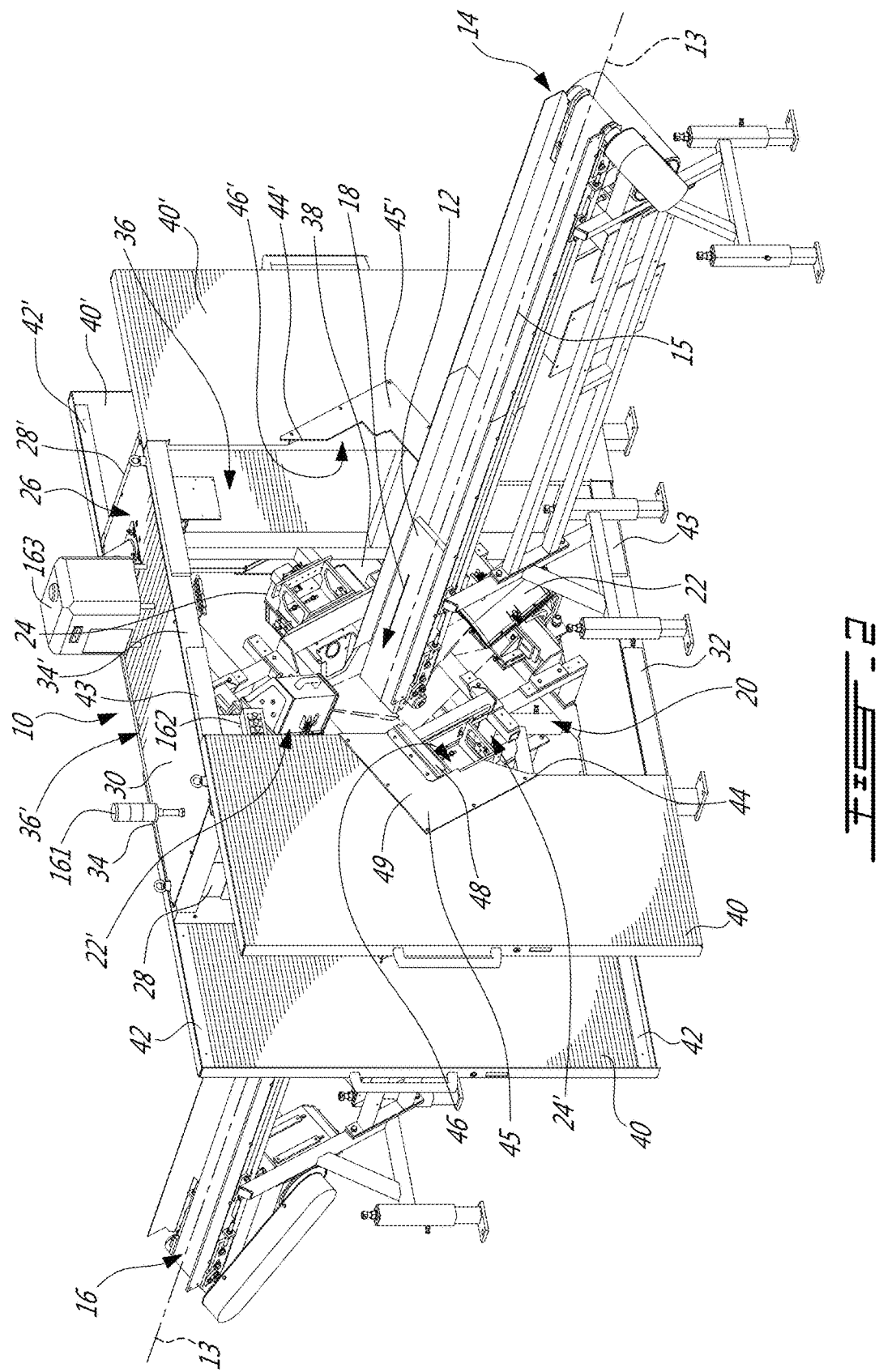
FIG. 2 is a perspective view of an example of laser scanning apparatus implementing the principle of the present invention and designed for simultaneously scanning four surfaces of an object, showing access doors provided on the apparatus enclosure in their open position.
Figure 3:
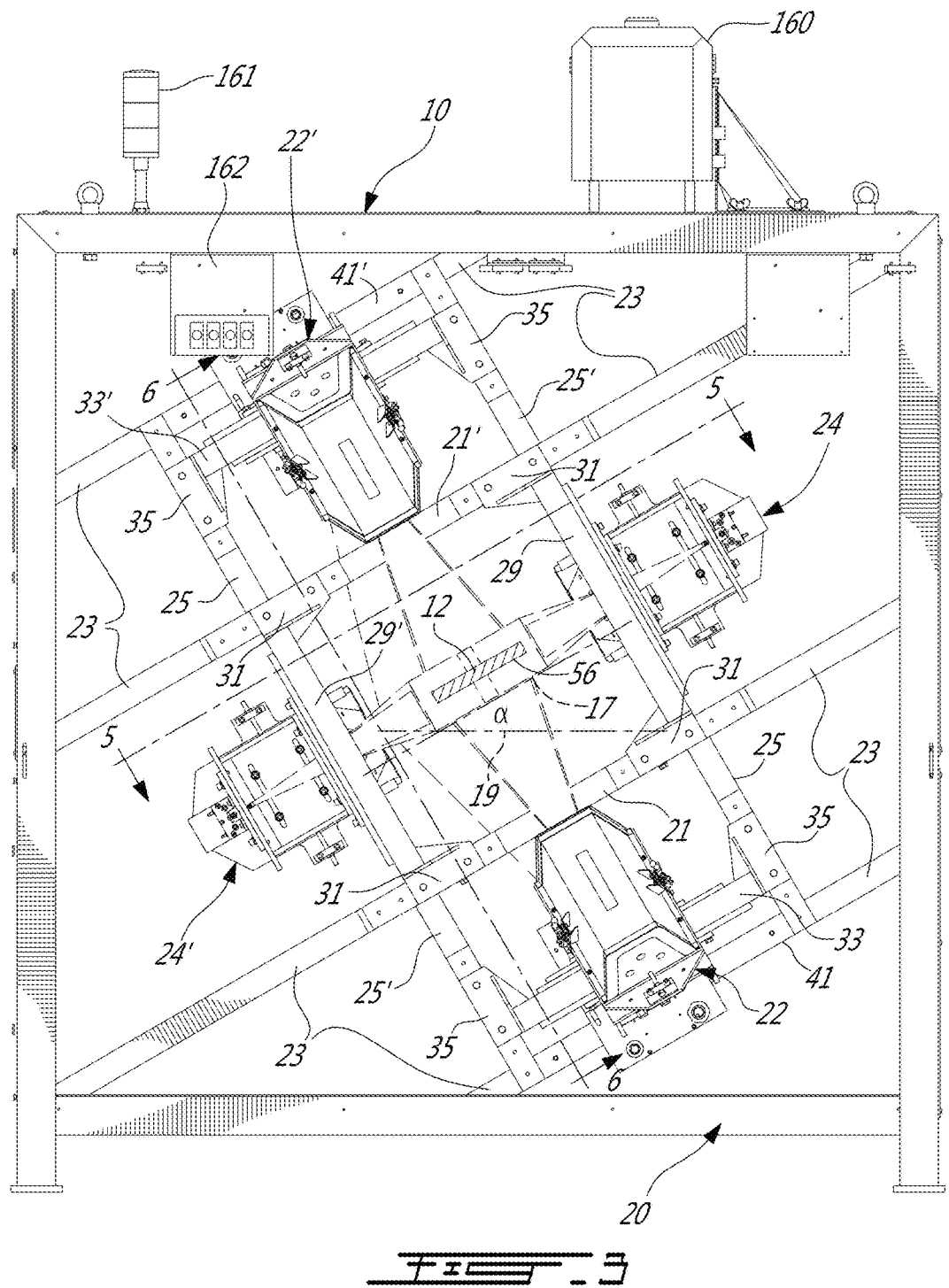
FIG. 3 is a front view of the apparatus of FIG. 2 with its access doors and conveyer units being not illustrated to better show the internal optical and mechanical components of the apparatus.

Referring now to FIG. 2 in view of FIG. 3, there is shown an example of optical scanning apparatus implementing the principle of the present invention and generally designated at 10, designed for simultaneously scanning four adjacent surfaces of an object 12, which is a wooden board to be inspected in the present example, employing four corresponding imaging sensor units 22, 22' and 24, 24' to generate reflection intensity images of the surface characteristics of the object. In the present example, the generated image data associated with board bottom surface 56, hereinafter designated as target image data, is likely to be defective due to adverse external condition to which one or more optical components as part of a first imaging sensor unit 22 are subjected. In typical industrial environments, such adverse external condition takes place when these optical components are exposed at various levels to soiling caused by dirt and dust which deposit with time on the outer surface of optical light transmission parts such as protecting glass for camera objective and light source, which soling acts as an optical mask affecting intensity of light transmitted therethrough.

The proposed image correction approach involves processing of the target image data by applying a correction calculated from a comparison between the reflection intensity image data associated with the target surface and reflection intensity image data associated with a reference surface, as generated by a second imaging sensor unit 22' having one or more optical components substantially not subjected to the adverse external condition. Then, the correction data are applied to the reflection intensity image data associated with the target surface to generate corrected intensity image data compensating for the adverse external condition. As will be described in detail below, according to an embodiment, the calculation of correction data involves image pixels corresponding to at least one reflection-based characteristic common to both target and reference surfaces and present over a major part thereof. Although the embodiments that will be described below make use of one or more lasers as light sources for purposes of imaging, any other appropriate light source of a fluorescent, incandescent, gas discharge or electroluminescent type may be used. In some embodiments, whenever a linear light source such as a laser is used to perform scanning, either raw image data or corrected images data may be filtered to reduce low frequency noise induced by such linear scanning, using a filtering method such as disclosed in U.S. published Patent application No. 2014/0307119 A1 naming the same applicant, the entire content of which document being incorporated herein by reference. Moreover, it will be appreciated by the person skilled in the art that the scanning apparatus 10, which will be described below in the context of a practical embodiment of the present invention, could be adapted to inspect objects of various nature, materials or shapes. The apparatus 10 according to the embodiment shown in FIG. 2 is capable of generating two complementary color image frames representing each one of the four surfaces of the object 12, from which reflection-related characteristics of the scanned surface can be detected, such as knots, mineral streaks, slits, heartwood and sapwood areas, as will be explained below in detail. As mentioned above, each one of color image frames can be processed to reduce low frequency noise. Furthermore, profile-related image data can be used to detect other board characteristics including geometrical and surface defects such as wane, holes, cracks etc., using known detection techniques such as disclosed in prior U.S. Pat. No. 8,502,180 and U.S. Pat. No. 6,122,065 naming the same applicant, the entire content of which documents being incorporated herein by reference. The detected characteristics are typically fed to a cut optimizer software providing a cutting solution into subdivided products from each board, producing an optimum yield in term of either economic value or material utilization. Any appropriate optimization approach can be used, including a one-axis or two-axis optimization approach such as described in U.S. Pat. No. 6,690,990 issued to the same applicant. For example, the apparatus 10 may be used by a furniture or floorwood manufacturing plant to increase production yields by upgrading wood products in view of raw wooden board quality and by minimizing the impact of any raw wood quality decrease upon profitability and performance of the manufacturing plant.

Figure 4:
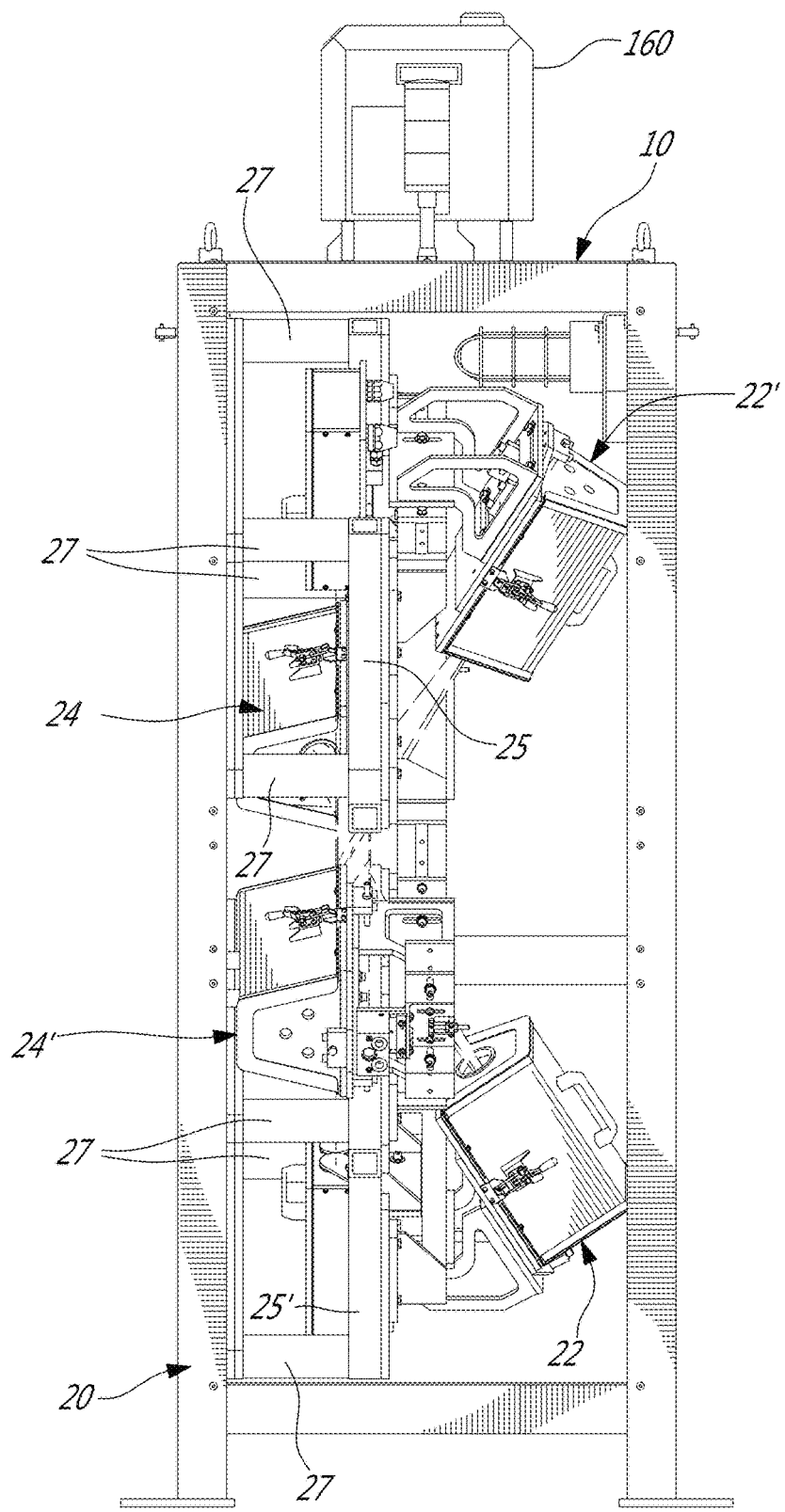
FIG. 4 is a side view of the apparatus of FIG. 2 with its enclosure wall and conveyer units being not illustrated to better show the internal optical and mechanical components of the apparatus.

Turning again to FIG. 2 in view of FIG. 3, the apparatus 10 has an infeed conveyer unit 14 and an outfeed conveyer unit 16 for moving the board 12 to be inspected through the apparatus along a travel path axis 13 in the direction of arrow 18. In the present embodiment, the transporting plane of each conveyer unit 14,16, which is designated at 17 on FIG. 3, is preferably at an angle α of about 30° with respect to a horizontal plane designated at 19 so that a fed board 12 is caused to urge under gravity against a guide 15 provided on each conveyer unit 14,16. However, conveyers for transporting boards according to another orientation such as parallel to the horizontal plane could also be used, by providing appropriate adaptation. In the example shown, the apparatus 10 is particularly adapted to receive wooden boards from wood processing equipment capable of machining top, bottom and both side surfaces of each board, for inspection thereof. The apparatus 10 is provided with a frame 20 on which are mounted laser-based imaging sensor units 22, 22' and 24, 24', using pairs of cross-bars 25, 25' and a further pair of cross-bars 21, 21', which cross-bars are secured to frame bars 23 through members 27 shown on FIG. 4. The imaging sensor units 24, 24' are adjustably held on cross-bars 21, 21' using support members 29, 29', bolted at both ends 31 thereof. Conveniently, the imaging sensor units 22, 22' are adjustably held on respective pairs of cross-bars 25, 25' using support members 33, 33' bolted at both ends 35 thereof. Further cross-bars 41, 41', are provided to strengthen the mounting arrangement. It is to be understood that any other configuration of mounting arrangement can be used to adjustably secure the imaging sensor units onto the apparatus frame 20. For safety purposes, the apparatus may include status indicating lights 161, and a panel 162 may be provided to indicate and allow control of operation status of the lasers used by the imaging sensor units 22, 22' and 24, 24'. A cooling system 163 may be provided to stabilize coherent light generation of the lasers by allowing cooling and temperature control thereof as will be described later in more detail in view of FIG. 10.

Referring again to FIG. 2, the apparatus 10 is protected and isolated from its working environment by an enclosure 26 having a peripheral portion formed by side walls 28, 28' top wall 30 and bottom wall 32 connected to the frame 20 and forming spaced apart front and rear peripheral edges 34, 34' defining a space in which the frame 20 and the imaging sensor units 22, 22' and 24, 24' are contained. Such known enclosure is disclosed in prior U.S. Pat. No. 8,723,945 B2 naming the same applicant, the entire content of which document being incorporated herein by reference. Conveniently, the enclosure 26 is provided at rear and front ends 36, 36' with pairs of access doors 40, 40' having outer closing edges 42, 42' adapted to mate with corresponding portions of the peripheral edges 34, 34', and inner closing edges 44, 44' adapted to mate one with another at first portions thereof, which, in the example shown, are located on the upper and lower parts of the doors 40, 40' and partially extend along opening plates 45, 45' provided thereon. As shown on FIG. 2, the peripheral edges 34 and 34' are conveniently provided at their respective upper and lower portions with holding rails 43 designed to engage corresponding upper and lower portions of the outer closing edges 42, 42' to allow sliding of access doors 40, 40' which are provided with bearings. It is to be understood that any other appropriate access door type, such as using hinges located on lateral portions of the peripheral edges 34, 34', could alternatively be used. The closing edges 44, 44' are provided with clearances 46, 46' to define a corresponding opening 38 whenever the access doors 40, 40' are brought one toward another from an open position as shown on FIG. 2 to a closing position, which opening 38 is aligned with the travel path axis 13 to allow the movement of board 12 through the apparatus 10.

For safety purposes, to minimize the risk that any reflected laser light leaks out through apparatus opening 38 and causes eye injury to plant operators, adjacent the clearance portion 46, the opening plate 45 is provided with a shielding element 48 attached to a holder 49 to confine reflections of the laser beams produced by the imaging sensor units 22, 22' and 24, 24' within the enclosure while allowing the movement of the board 12. The shielding element 48 may be made of any appropriate material, and preferably of a flexible material such as plastic, rubber or fabric, in any appropriate form such as a strip, curtain or brush, as a unitary piece or constituted of a plurality of elements such as fibres, provided it is sufficiently opaque to laser light. Optionally, for providing adaptation to various board dimension values (thickness in the example shown), the shielding element 48 may be rendered adjustable with respect to the closing edges 44 by providing the holder 49 with an appropriate mechanism, especially in a case where the material of which the shielding element is made is rigid, to minimize gaps through which reflected laser light may leak out, while ensuring unrestricted passage of boards through the apparatus.

A particular compact arrangement of the imaging sensor units as part of the apparatus 10 of the present example will now be described in detail with reference to the schematic sectional views of FIGS. 5 and 6. It can be seen that the conveyer units 14 and 16 are respectively provided with conveyer rolls 37, 37' which define, in the example shown, the limits of an inspection area 50 located at a central plane designated at 52 which is transverse to the travel path axis 13, and equidistant to the conveyer rolls 37 and 37'. It can be appreciated that the spacing between conveyer rolls 37 and 37' determines the minimum length a board 12 must have in order to be longitudinally transported through the inspection apparatus. Therefore, in order to accept a wide range of board lengths (in direction of Y axis on the reference system 39), the conveyer rolls spacing has to be minimized, while leaving the optical clearance required by the scanning of board of various widths (in direction of X axis on the reference system 39). The width of the transporting surface of the conveyer units 14 and 16, starting from the guide 15, is made sufficient to provide board feeding adaptation to boards of various width values, up to the largest board width limit indicated in dotted lines 30 adjacent the imaging sensor unit 24 also represented in dotted lines on FIG. 5. It is to be understood that in any case where the conveyers for transporting boards 12 are designed to work without a guide 15 extending within the adjacent to the inspection area 50, for example according to another orientation such as parallel to the horizontal plane, the conveyer width may extend on the other side of the travel path axis 13 toward imaging sensor unit 24', up to a further board width limit as indicated by dotted line 30'.

It can be seen from FIG. 6 that the first imaging sensor unit 22 represented in dotted lines includes a first digital camera 51 having a first optical sensing field 53 directed toward the travel path axis 13 and defining a first scanning zone 54 associated with a first, target board surface 56 (bottom surface in the example shown) as intersected by the first sensing field 53. A detailed description of a first imaging sensor unit 22 according to the present example of scanning apparatus will be provided below in view of FIGS. 8 to 10. A digital 3D camera such as model C3-2350 from Automation Technology Gmbh (Germany) may be used. In one embodiment, the first imaging sensor unit 22 also includes a linear laser source 58 associated with a characteristic wavelength for directing at an angle with the first sensing field 53 a linear-shaped laser beam 55 toward the scanning zone 54 to form a reflected laser line 60 onto the object bottom surface 56, as shown in FIG. 5 in dotted lines. The laser beam 55 defines an associated scanning plane transverse (within plane X-Z in reference system 39) to the travel path axis 13 in the example shown. Accordingly, the digital camera 51 having its sensing field 53 intersected by the board target surface 56 onto which laser line 60 is reflected, the latter is captured by the camera 51 which is configured to generate reflection intensity image data associated to the target surface 56. For example, the laser wavelength can be selected within a red wavelength range, such as from about 620 to 660 nm. The fan angle of the laser source 58 may be chosen so that sufficient reflected beam intensity is obtained on board surface 56 in scanning zone 54, to be properly captured by the camera used. A 630 nm compact laser from Osela Inc. (Pointe-Claire, Quebec, Canada) with transverse fan angle of about 30° may be used to obtain sufficient reflected beam intensity when the apparatus 10 shown in FIGS. 2 to 6 is used. It is to be understood that any other appropriate laser available in the marketplace can be used. It can be appreciated that, for the present example embodiment involving a particular adverse external condition, the generally upward orientation of the first sensing field 53 and laser beam 55 associated with the first imaging sensor unit 22 substantially promotes deposit and adhesion of dirt and dust onto its optical components, so that a significant level of soiling may occur with time. Accordingly, either the intensity of light directed to the inspected target surface 56 or the intensity of reflected light reaching the first digital camera 51, or both, may be affected with time, thereby providing optical scanning which generates reflection intensity image data likely to be more or less representative of the actual reflection-based characteristics of the scanned target surface.

Referring now to in FIG. 7, the apparatus 10 is provided with a laser control device 71 receiving through line 111 exposure control signal from camera 51 and operatively connected through lines 156 to the laser source 58 for activating thereof.

Turning again to FIG. 6, in a dual laser embodiment, the first imaging sensor unit 22 also includes a further linear laser source 59, which is designated by dotted reference numeral line to indicate that it is adjacently disposed behind linear laser source 58 in the schematic representation shown. It is to be understood that the respective positions of the laser sources 58, 59 may be permutated so that the laser source 58 would be behind the laser source 59, without changing the operation principle of the imaging sensor unit 22. Such permutation is shown in the example described below in reference to FIGS. 8 to 10. In that embodiment, the further linear laser source 59 is characterized by a distinct laser wavelength, for directing at an angle with the first sensing field 53 a further linear-shaped laser beam 67 toward the scanning zone 54 to form a further reflected laser line 160 onto the object bottom surface 56, at substantially a same position as the laser line 60 shown in FIG. 5. Turning back to FIG. 6, the further linear laser source 59 defines an associated scanning plane transverse to the travel path axis 13 in the example shown, which is the same as the plane defined by the linear laser source 58, and the further laser beam 67 is thus designated by a dotted reference numeral line to indicate that it is coplanar with the laser beam 55 in the schematic representation shown. In other words, for the apparatus of the that embodiment, the linear laser sources 58, 59 may be disposed so that their respective laser beams 55, 67 share a same scanning plane extending transversely to travel path axis 13. In order to project their respective beams toward the same target scanning zone 54, in a substantially same direction and orientation within the common scanning plane, the linear laser sources 58, 59 are adjacently disposed so that their linear-shaped beams are aligned within the scanning plane and extend sufficiently to cover the entire target scanning zone 54, as will be described later in more detail with reference to FIG. 9. Is to be understood that any other appropriate optical configuration may be used to have the laser sources 58, 59 projecting their respective beams toward the same target scanning zone 54.

Furthermore, the linear laser sources 58, 59 may be adjacently disposed at a substantially same distance from the scanning zone 54. In the present example, the laser wavelength of further source 59 can be selected within a green wavelength range, such as from about 510 to 540 nm. Here again, the fan angle of the further linear laser source 59 may be chosen so that sufficient reflected beam intensity is obtained on board surface 56 in scanning zone 54, to be properly captured by the camera used.

Conveniently, the linear laser sources 58, 59 are characterized by respective fan angles selected to produce substantially same level of light intensity at the scanning zone 54. A 515 nm laser such as model 3R 100-0037 from Osela inc. (Pointe-Claire, Quebec, Canada) with transverse fan angle of about 10° may be used to obtain sufficient reflected beam intensity for the apparatus shown in FIGS. 2 to 6. It is to be understood that any other appropriate linear laser available in the marketplace can be used. Here again, the digital camera 51 having its sensing field 53 intersected by the board surface 56 onto which further laser line 160 is reflected, the latter is captured by the camera 51, alternately with the reflected laser line 60, to produce interlaced sequences of reflection intensity image data, as the board is conveyed through the scanning unit. Turning again to FIG. 7, the laser control device 71 of the apparatus 10 according to the dual laser embodiment is also operatively connected through line 158 to the further laser source 59 so as to activate laser sources 58, 59 alternately according to a predetermined frequency.

Turning back to FIG. 6, the first imaging sensor unit 22 is provided with a data processing module 57 programmed to generate, along with the reflection intensity image data, output data related to the profile of the board bottom surface 56 through triangulation ranging, which profile is associated with a reference axis (axis Z in reference system 39) orthogonal to a reference plane (plane X-Y in reference system 39) parallel to the travel path axis. In the single laser embodiment, the digital camera 51 is configured to capture two-dimensional images of the reflected laser lines 60 formed by the laser beam 55 onto the board bottom surface 56, from which images the data processing module 57 derives the profile-related output, involving calculation of the center of gravity of the laser beam image, or any other appropriate algorithm. In the dual laser embodiment, the digital camera 51 is configured to capture alternately two-dimensional images of the first and second reflected laser lines 60, 160 formed by the laser beams 55 and 67 onto the board bottom surface 56, from which images the data processing module 57 derives the profile-related output. For example, the imaging sensor unit may use a same laser triangulation ranging approach as disclosed in U.S. Pat. No. 7,429,999 issued to same applicant, the entire content of which document is incorporated herein by reference. Conveniently, the reflection intensity image data may be derived by integration of the measured intensity under the transverse laser line profile, i.e. extending transversely to the travel path axis 13, which transverse profile can be delimited on both side of its peak by applying a minimum intensity threshold. It is to be understood that any other appropriate technique can be used to generate the reflection intensity image data. The processing module 57 can be wholly or partially integrated into the digital camera 51, or be part of a computer system interfaced with the camera to receive and process raw image signals.

Referring again to FIG. 6 in view of FIG. 5, the second imaging sensor unit 22' represented in dotted lines includes a second digital camera 51' having a second optical sensing field 53' directed toward the travel path axis 13 and defining a second scanning zone 54' associated with a second board surface 56' (top surface in the example shown) as intersected by the third sensing field 53', which board surface 56' is used as a reference surface for purposes of correction data calculation, as will be explained below in detail. According to an embodiment of the scanning apparatus, the second imaging sensor unit 22' may be identical to the first imaging sensor unit 22, as will be described below in view of FIGS. 8 to 10. A same digital 3D camera such as the one provided on first imaging sensor unit 22 may be used, and similarly, in the single laser embodiment, the second imaging sensor unit 22' includes a laser source 58' associated with the characteristic laser wavelength for directing at an angle with the second sensing field 53' a linear-shaped laser beam 55' toward the scanning zone 54' to form a reflected laser line 60' onto the object reference surface 56', as shown in FIG. 5. The laser beam 55' defines an associated scanning plane transverse (within plane X-Z in reference system 39) to the travel path axis 13 in the example shown. Accordingly, the digital camera 51' having its sensing field 53' intersected by the reference surface 56' onto which the laser line 60' is reflected, the latter is captured by the camera 51' which is configured to generate reflection intensity image data associated with the reference surface 56', in a same manner as explained above regarding operation of camera 51, and a same model of laser such as the one provided on first imaging sensor unit 22 may be used. It can be appreciated that, for the present example embodiment involving a particular adverse external condition, the generally downward orientation of the second sensing field 53' and laser beam 55' associated with the second sensor unit 22', substantially prevents dirt and dust to deposit on and adhere onto its optical components, so that no significant level of soiling occurs. Accordingly, neither the intensity of light directed to the inspected reference surface 56', nor the intensity of reflected light reaching the second digital camera 51' are affected, thereby providing optical scanning which generates reflection intensity image data likely to be substantially representative of the actual reflection-based characteristics of the scanned reference surface.

Turning again to FIG. 6, in the dual laser embodiment, the second imaging sensor unit 22' also includes a further laser source 59', which is designated by dotted reference numeral line to indicate that it is adjacently disposed behind laser source 58' in the schematic representation shown in FIG. 5. The further laser source 59' is characterized by the same laser wavelength as associated with further laser source 59, for directing at an angle with the sensing field 53' a further linear-shaped laser beam 67' toward the scanning zone 54' to form a further reflected laser line 160' onto the reference surface 56', as shown in FIG. 5. The further laser source 59' defines an associated scanning plane transverse to the travel path axis 13 in the example shown, which is the same as the plane defined by the laser source 58', and the further laser beam 67' is thus designated by dotted reference numeral line to indicate that it is coplanar with the laser beam 55' in the schematic representation shown. Here again, the fan angle of the further laser source 59' may be chosen so that sufficient reflected beam intensity is obtained on reference surface 56' in scanning zone 54', to be properly captured by the camera used. Here again, the digital camera 51' having its sensing field 53' intersected by the reference surface 56' onto which the further laser line 160' is reflected, the latter is captured by the camera 51', alternately with the first reflected laser line 60', to produce interlaced sequences of reflected laser intensity image data, by means of laser control device 71' as shown in FIG. 7 in accordance with the dual laser embodiment, operatively connected to the laser sources 58', 59' for activating thereof alternately according to the predetermined frequency.

Turning back to FIG. 6, the second imaging sensor unit 22' is also provided with a data processing module 57 programmed to generate, along with the reflection intensity image data, output data related to the profile of the reference surface 56' through triangulation ranging, in a same manner as explained above regarding the operation of first imaging sensor unit 22. In the single laser embodiment, the digital camera 51' is configured to capture two-dimensional images of the reflected laser lines 60' formed by the laser beams 55' onto the reference surface 56', from which image the data processing module 57 derives the profile-related output, involving calculation of the center of gravity of the laser beam image as explained above. In the dual laser embodiment, the digital camera 51 is configured to capture alternately two-dimensional images of the first and second reflected laser lines 60', 160' formed by the laser beams 55' and 67' onto the board bottom surface 56', from which images the data processing module 57 derives the profile-related output. The reflection intensity image data may be derived by integration of the measured intensity under the transverse laser line profile, in a same manner as performed by the first imaging sensor unit 22. Here again, the processing module 57 can be wholly or partially integrated into the digital camera 51', or be part of a computer system interfaced with the camera to receive and process raw image signals.

While the proposed inspection apparatus may be basically used to scan two opposed surfaces, namely target (bottom) and reference (top) surface a board by means of imaging sensor units 22 and 22', as mentioned above, the embodiment shown in FIGS. 2 to 6 is capable of simultaneously scanning four surfaces of an object, such as a wooden board also having first and second side surface 66, 66', both of which being adjacent to target and reference surfaces 56, 56'. For so doing, third and fourth imaging sensor units 22' and 24' are provided according to a symmetrical configuration as compared to that which involves profile units 22 and 24 described above.

Turning back to FIG. 5, there is shown a third imaging sensor unit 24 represented in dotted lines including a third digital camera 61 having a third optical sensing field 63 directed toward the travel path axis 13 and defining a third scanning zone 64 associated with the third board surface 66 (left side in the example shown) adjacent to reference board surface 56', the third scanning zone 64 being intersected by the third sensing field 63. According to an embodiment of the scanning apparatus, the mechanical design of the third imaging sensor unit 24 may be similar to the one disclosed in U.S. Pat. No. 8,723,945 B2 in view of FIGS. 10 to 11 thereof, naming the same applicant, the entire content of which document being incorporated herein by reference. A digital 3D camera such as model C3-2350 from Automation Technology Gmbh (Germany) may also be used, preferably provided with a "Scheimpflug" adapter for amplifying the optical depth of field of the imaging sensor unit 24 to provide inspection capability of the apparatus to boards of various widths, as will be described later in more detail. In the embodiment shown, the third imaging sensor unit 24 includes a single laser source 68 directing at an angle with the second sensing field 63 a linear-shaped laser beam 65 toward the scanning zone 64 to define an associated scanning plane transverse (within plane X-Z in reference system 39) to the travel path axis 13. For products such as flooring wood, side surfaces are not intended to be visible in use, and obtaining two complementary color image frames to detect aesthetical surface characteristics such as heartwood and sapwood areas, may not be necessary. In these cases, the reflected laser intensity image data can be obtained from single-color image frames. However, although the second imaging sensor unit 24 according to the embodiment shown in FIG. 5 uses a single linear laser source 68, it is to be understood that a pair of laser sources as provided on the first imaging sensor 22 of FIG. 6 could be used in another embodiment. A similar laser source as either of those provided on the first imaging sensor unit 22 may be used, with a transverse fan angle of about 10°. The second imaging sensor unit 24 is also provided with a data processing module 57 programmed to generate, along with the reflection intensity image data, output data related to the profile of the board edge surface 66 through same triangulation ranging approach employed by the first imaging sensor unit 22, which profile is in this case associated with a reference axis (axis X in reference system 39) orthogonal to a reference plane (plane Z-Y in reference system 39) parallel to the travel path axis 13.

Referring again to FIG. 6 in view of FIG. 5, it can be appreciated that the second and third imaging sensor units 22', 24 in the embodiment shown are conveniently disposed one with respect to another so that their respective second and third scanning zones 54', 64 are sufficiently spaced one with another along the travel path axis 13 to substantially prevent mutual scanning interference between second and third imaging sensor units 22', 24. In the example shown, since second (top) and third (left side) surfaces 56', 66 are adjacent one with another, the scanning plane associated with laser beams 55' and 67' and the scanning plane associated with the laser beam 65 are offset by a distance "d" in order to prevent illumination interference that would otherwise be caused by laser beams 55' and 67' in scanning zone 54' on the camera 61 of imaging sensor unit 24, and reciprocally by laser beam 65 in scanning zone 64 on the camera 51' of imaging sensor unit 22'. It can be appreciated that although simultaneous scanning of the profile of the adjacent surfaces 56', 66 may be carried out, the first and second scanning planes being non coplanar due to the offset distance "d", the scanned areas on adjacent surfaces are consequently not coplanar with respect to the reference axis (axis Y on the reference system 39) parallel to the travel path axis 13. Therefore, there is a need for assembling respective output data generated by imaging sensor units 22' and 24, with corresponding data representing location along the travel path axis. A method for that purpose, which is based on the fact that the board is moving at known speed or position/time data along the travel path axis, is described in U.S. Pat. No. 8,193,481 B2 naming the same applicant, the entire content of which document being incorporated herein by reference. It is to be understood that any other appropriate data assembling technique can be used.

Furthermore, to provide a compact arrangement of second and third imaging sensor units 22' and 24, it can also be appreciated in the example illustrated on FIGS. 5 and 6, that the second sensing field 53' is crossing the central plane 52 toward the laser beams 55' and 67', whereas the second sensing field 63 is crossing the central plane 52 toward the laser beam 65. According to the imaging sensor configuration shown on FIGS. 5 and 6, the laser beams 55' and 67' are alternately directed toward the second scanning zone 54' within their associated scanning plane, and similarly, the laser beam 65 is directed toward the third scanning zone 64 within its associated scanning plane. This configuration allows minimizing the conveyer rolls spacing at a value near offset distance "d" while providing the optical clearance required by the scanning of boards within the desired ranges of board widths and lengths. In the example shown, the first (bottom) and second (top) surface 56, 56' are respectively target and reference surfaces associated with a first dimension (width) transverse to the travel path axis 13 and of a value selected from a first range of dimension values. The third surface 66 is a side (left) surface associated with a second dimension (thickness) transverse to the travel path axis 13 and of a value selected from a second range of dimension values. According to the proposed compact configuration, the second optical sensing field 53' has a depth adapted to define the second scanning zone 54' for any selected value of second dimension (thickness), whereas the third optical sensing field 63 has a depth adapted to define the third scanning zone 64 for any selected value of first dimension (width).

According to an alternate configuration of imaging sensor units (not shown), the second sensing field 53' may be directed toward the travel path axis 13 within its associated scanning plane (along Z axis of reference system 39), and similarly, the third sensing field 63 may be directed toward the travel path axis 13 within its associated scanning plane. In that case, a similar compact arrangement can be obtained if the laser beams 55' and 67' are crossing the central plane toward the second sensing field 53', whereas the laser beam 65 is crossing the central plane toward the third sensing field 63.

Turning back to FIG. 5, there is provided in the embodiment shown a fourth imaging sensor unit 24' as represented in dotted lines includes a further digital camera 61' having an optical sensing field 63' directed toward the travel path axis 13 and defining a scanning zone 64' associated with a fourth board surface 66' (right side in the example shown) adjacent to first (bottom) board surface 56, the scanning zone 64' being intersected by the sensing field 63'. According to an embodiment of the scanning apparatus, the mechanical design of the fourth imaging sensor unit 24' may be similar to the one used by third imaging sensor unit 24 as described above, and a same digital 3D camera model provided with a "Scheimpflug" adapter can also be used. Similarly, the fourth imaging sensor unit 24' according to the embodiment shown includes a single laser source 68' directing at an angle with the sensing field 63' a linear-shaped laser beam 65' toward the scanning zone 64' within its associated scanning plane transverse (within plane X-Z in reference system 39) to the travel path axis 13. A same laser model such as provided on second imaging sensor unit 24 may be used. The fourth imaging sensor unit 24' is also provided with a data processing module 57 programmed to generate, along with the reflection intensity image data, output data related to the profile of the fourth board surface 66' through same triangulation ranging approach employed by the second imaging sensor unit 24, which profile being also associated with the reference axis X in reference system 39 orthogonal to the reference plane parallel to the travel path axis 13.

Referring again to FIG. 6 in view of FIG. 5, it can be appreciated that the first and fourth imaging sensor units 22, 24' are also disposed one with respect to another so that their respective scanning zones 54, 64' are sufficiently spaced one with another along the travel path axis 13 to substantially prevent mutual scanning interference between first and fourth imaging sensor units. Here again, there is a need for assembling respective output data generated by imaging sensor units 22 and 24', with corresponding data representing location along the travel path axis 13. In the example shown, since first (bottom) and fourth (right side) surfaces 56, 66' are adjacent one with another, the scanning plane associated with the laser beams 55 and 67 and the scanning plane associated with the laser beam 65' are also offset by a distance "d" in order to prevent illumination interference that would otherwise be caused by either laser beam 55 or 67 in scanning zone 54 on camera 61' of imaging sensor unit 24' (as well as on camera 61 of imaging sensor unit 24), and reciprocally by laser beam 65' in scanning zone 64' on camera 51 of imaging sensor unit 22 (as well as on camera 51' of imaging sensor unit 22'). Furthermore, to provide a similar compact arrangement as obtained with the second and third imaging sensor units 22 and 24 described above, it can also be appreciated in the example illustrated on FIGS. 5 and 6, that the sensing field 53' of first imaging sensor unit 22 is crossing the central plane 52 toward the laser beam 55, whereas the sensing field 63' of the fourth imaging unit 24' is crossing the central plane 52 toward the laser beam 65'. To provide compactness and optical clearance in same manner as performed by imaging sensor units 22' and 24 as explained above, the laser beams 55 and 67 are alternately directed toward the scanning zone 54 within their associated scanning plane, and similarly, the laser beam 65' is directed toward the second scanning zone 64' within its associated scanning plane. In the example shown, opposite to the side surface 66, the fourth surface 66' is the other side (right) surface associated with the second dimension (thickness) transverse to the travel path axis 13 and of a value selected from the second range of dimension values. Here again, according to the proposed compact configuration, the optical sensing field 53' has a depth adapted to define the scanning zone 54' for any selected value of second dimension (thickness), whereas the optical sensing field 63' has a depth adapted to define the scanning zone 64' for any selected value of first dimension (width).

In the example shown on FIGS. 5 and 6, for the sake of simplicity, the scanning planes associated with the first and second imaging sensor units 22, 22' are substantially coplanar, whereas the scanning planes associated with the third and fourth imaging sensor units 24, 24' are substantially coplanar. For so doing, the laser beams 55 (and 67 in the dual laser embodiment) and 55' (and 67' in the dual laser embodiment) are conveniently oriented toward target (bottom) and reference (top) surfaces 56, 56' respectively, in aligned and opposed directions. Similarly, the laser beams 65, 65' are oriented toward third and fourth (side) surfaces 66, 66', respectively, in aligned and opposed directions. However, it is to be understood that any other appropriate configuration of scanning planes may be employed. According to an alternate configuration of the imaging sensor units (not shown), the first sensing field 53 may be directed toward the travel path axis 13 within its corresponding scanning plane, and similarly, the fourth sensing field 63' could be directed toward the travel path axis 13 within its corresponding scanning plane. In that case, a similar compact arrangement may be obtained if the laser beams 55, 67 are crossing the central plane toward the sensing field 53, whereas the laser beam 65' is crossing the central plane toward the sensing field 63'.

Referring now to FIGS. 8 and 9, there is illustrated an example of mechanical design for the imaging sensor unit 22, which can be also applied to imaging sensor unit 22', to be provided on the inspection apparatus described above in view of FIGS. 2 to 8, which FIGS. 8 and 9 shows a camera enclosure assembly generally designated at 70 and shown without its cover, which may be of the same design as disclosed in U.S. Pat. No. 8,708,582 B2 naming the same applicant, the entire content of which document being incorporated herein by reference. The camera enclosure assembly includes an enclosure body 72 adapted to be secured to the apparatus frame through a mounting arrangement generally designated at 105, as better shown on FIG. 9. The mounting arrangement 105 has a back mounting plate 112 joined to lateral walls 113, 114 disposed in parallel spaced relationship and secured to a base mounting plate 115. As better seen from FIG. 9, the lateral walls 113, 114 are designed so that the back mounting plate 112 and the base mounting plate 115 form one with another a preset angle which is related to the angle at which the laser source 58 (and 59 in the dual laser embodiment) directs with respect to the optical sensing field 53 the linear-shaped laser beam 55 (and 67 in the dual laser embodiment) toward the scanning zone 54. The base mounting plate 115 is provided with elongate apertures 123 for receiving bolts 126 providing position adjustment along axis Y on reference system 39, and is also adapted to be adjustably secured to a rail 117 using an intermediary plate 118 designed to fit onto a central groove 121 provided on the rail 117 for rough position adjustment along axis X of reference system 39. The rail 117 is in turn attached to the support member 33 for the imaging sensor unit 22 (or member 33' for unit 22' shown in FIG. 3), whose ends 35 are attached to the cross-bars 25, 25' secured to frame bars 23 through members 27 as described above with reference to FIG. 3 in view of FIG. 4. As shown in FIG. 9, adjustably secured under support member 33 is a bottom plate 116 adapted to receive a mounting plate 125 having elongate openings for bolts (not shown), for lateral adjustment and securing of a flanged element 120 mechanically coupled to a device 122 for securing the laser assembly generally designated at 130, which includes laser source 58 in the single laser embodiment or the arrangement of laser sources 58, 59 in the dual laser embodiment, and for orienting thereof according to the desired angular direction with respect to the optical sensing field 53 and scanning zone 54, which laser assembly 130 will be described below in more detail with reference to FIG. 10. It can be seen from FIG. 8 that the mounting device 80 as provided on enclosure body 72 has a lateral plate 86 designed for maintaining adjustment of a lens assembly 95 coupled to a camera 51 (or 51') not provided with a "Scheimpflug" adapter, as opposed to cameras 61, 61' provided on the third and fourth imaging sensor units 24, 24' referred to above, which camera 51 is mounted within the enclosure body 72 such that it has its optical sensing field 53 directed toward opening 76, with an enclosure front end wall 74 arranged so that a protecting optical element 78 extends in a plane perpendicular to the central direction of the optical sensing field 53. However, the lateral walls 113, 114 being designed according to a preset angle related to the angle at which the laser source 58 (and 59 in the dual laser embodiment) directs with respect to the optical sensing field 53 the linear-shaped laser beam 55 (and 67 in the dual laser embodiment) toward the scanning zone 54, the enclosure front end wall 74 is secured at right angle to the base wall 84 without the need of wedges in the example shown.

As shown on FIG. 9, the enclosure assembly 70 is provided with a device 101 for displacing the enclosure body 72 in a direction (along axis X in reference system 39) perpendicular to the profile reference axis (axis Z in reference system 39) and parallel to the scanning plane (corresponding to the common plane of laser beams 55, 67 in the dual laser embodiment) to adjust the position of the optical sensing field with respect to the scanning plane. As shown on FIG. 9 in view of FIG. 8, the base wall 84 is secured to an intermediate plate 99 provided on the enclosure assembly 70, a laterally protruding portion of which plate having a pair of flanged elements 100 as part of device 101, each of which receiving a bolt 102 adapted to engage a corresponding threaded bore provided on lateral wall 113, 114 of the mounting arrangement 105. Cooperating with guiding and securing bolts 107 engaging elongate apertures 127 provided on back mounting plate 112 forming a wide aperture 128 to lodge the device 101 as shown on FIG. 8, the device 101 allows fine adjustment of the position of enclosure body 72 along axis X in reference system 39 relative to the back mounting plate 112. It is to be understood that the adjustment device 101 may be provided on any other appropriate location with respect to the enclosure body, and that any other appropriate type of mechanical or electromechanical adjustment device can be used.

As shown on FIG. 8, the intermediate plate 99 provided on the enclosure assembly 70 has at rear end thereof a protruding portion having a flanged element 108 as part of a further device 110 mechanically coupled to the enclosure body 72 for displacing thereof in a direction transverse to axis X in reference system 39 to further adjust the position of the optical sensing field with respect to the scanning plane. For so doing, the flanged element 110 receives a bolt 109 adapted to engage a corresponding threaded bore provided on rear end wall 82. Cooperating with guiding and securing bolts 104 engaging elongate apertures (not shown) provided on base wall 84, the device 110 allows fine adjustment of position of the enclosure body 72 transversely to axis X in reference system 39 relative to the intermediate plate 99. It is to be understood that the adjustment device 110 may be provided on any other appropriate location with respect to the enclosure body, and that any other appropriate type of mechanical or electromechanical adjustment device can be used.

Turning now to FIG. 10, the laser assembly 130, will be now described in detail. As part of the laser securing device 122 is a back plate 132 adjustably mounted on the flanged element 120 using set screws 133 passing through elongate apertures 134 provided on back plate 132. The back plate is adapted to receive a laser mounting plate 136 through an intermediary cooling plate 138 made of a thermally conductive metal, as part of the cooling system 163 referred to above in view of FIG. 2, and whose function is to stabilize coherent light generation of the laser source 58 (and 59 in the dual laser embodiment) by allowing cooling and temperature control thereof. Set screws 139 are used to secure the mounting plate to the cooling plate 138, which is in turn secured to the back plate 132 using set screws 141. The cooling system further includes a cooling fluid flow circuit in fluid communication with inlet 142 and outlet 144 of collector 137 and integrated within a central portion of the back plate 132, and in thermal contact with the cooling plate 138, the latter being thermally insulated from the peripheral portion of the back plate using an adaptor 140 made of a proper thermal insulating material and secured to the back plate 132 using set screws 143. The body of collector 137 is hermetically affixed to upper portion of back plate 132 using screws 135, and is operatively connected to cooling fluid source as part of the cooling system though input and return lines (not shown) using couplings 145. The back plate 132 may be provided with sleeves 146 to gather the power supply and data lines connected to the laser source 58 (and 59 in the dual laser embodiment) and a connector 148 may be provided to receive output lines of temperature probes (not shown) enabling temperature control. According to an embodiment, in order to project their respective beams toward the same target scanning zone 54, in a substantially same direction and orientation within the common scanning plane, the laser sources 58, 59 as part of dual laser assembly 130 of the dual laser embodiment can be adjacently disposed so that their linear-shaped beams 55, 67 as shown in FIG. 9 are aligned within the scanning plane and extend sufficiently to cover the entire target scanning zone 54, corresponding to the overlapping portions of laser beams 55 and 67 as designated at 73, while an extraneous portion 75 of laser beam 55 extends beyond the scanning zone 54 in the example shown, which extraneous portion 75 is not intersected by a board surface to be scanned. Turning back to FIG. 10, according to the dual laser embodiment, the proposed adjustment of direction and orientation of the laser sources 58, 59 can be obtained by making one of these laser sources stationary with respect to the mounting plate 136, while the other is made capable of being adjusted relative to the stationary laser source. In the example shown in FIG. 10, the second (green) laser source 59 is chosen to be stationary, while the first (red) laser source 58 allows adjustment through an appropriate support arrangement. For so doing, the casing 77 of laser source 59 is directly secured to the mounting plate 136 in a vertical position with its control connector 147 and power supply line 149 extending upwardly. In turn, the body portion of first laser source 58 is received within a channel provided on a support block 79, so that control line 129 and power supply line 131 of laser source 58 extend upwardly. The support block 79 is itself adapted to be received in a holder 83 secured to mounting plate 136 and providing position adjustment for the support block 79 through four screw and spring assemblies adapted to engage with corresponding holes 103 on support block 79. The laser assembly 130 may be contained for isolation from working environment in an enclosure 151 whose bottom wall 153 is provided with a pair of upper sockets 155 cooperating with lower sockets 157 to receive protective glasses 159 adapted to provide free transmission of the laser beams without distortion. A pair of pivoting shutters 165 may be provided, which can be brought in a beam closing position for safety purposes whenever operation of the scanning apparatus is interrupted to allow an intervention by the operator. In the case where a third laser source, e.g. blue laser, would be included in the imaging sensor unit, the mounting plate 136 could be designed to receive that additional laser source, and an additional protective glass and shutter could be mounted on the enclosure 151.

Turning back to FIG. 7, the apparatus 10 further includes data processing means that can be in the form of a computer 69 provided with suitable memory and proper data acquisition interface to receive through line 168 the interlaced sequences of reflection intensity image data generated by cameras 51, 51'. In the dual laser embodiment, the computer is further programmed for separating the interlaced sequences of reflection intensity image data produced according to camera timing sequence 150, to generate two complementary color image frames representing each scanned board surface, according to alternate timing sequences 152, 154, as will be explained below in view of FIG. 11. Although the computer 69 may conveniently be a general-purpose computer, an embedded processing unit such as based on a digital signal processor (DSP), can also be used to perform image frames generation. It should be noted that the present invention is not limited to the use of any particular computer, processor or digital camera as imaging sensor for performing the processing tasks of the invention. The term "computer", as that term is used herein, is intended to denote any machine capable of performing the calculations, or computations, necessary to perform the tasks of the invention, and is further intended to denote any machine that is capable of accepting a structured input and of processing the input in accordance with prescribed rules to produce an output. It should also be noted that the phrase "configured to" as used herein regarding electronic devices such as computer or digital camera, means that such devices are equipped with a combination of hardware and software for performing the tasks of the invention, as will be understood by those skilled in the art.

Figure 11:
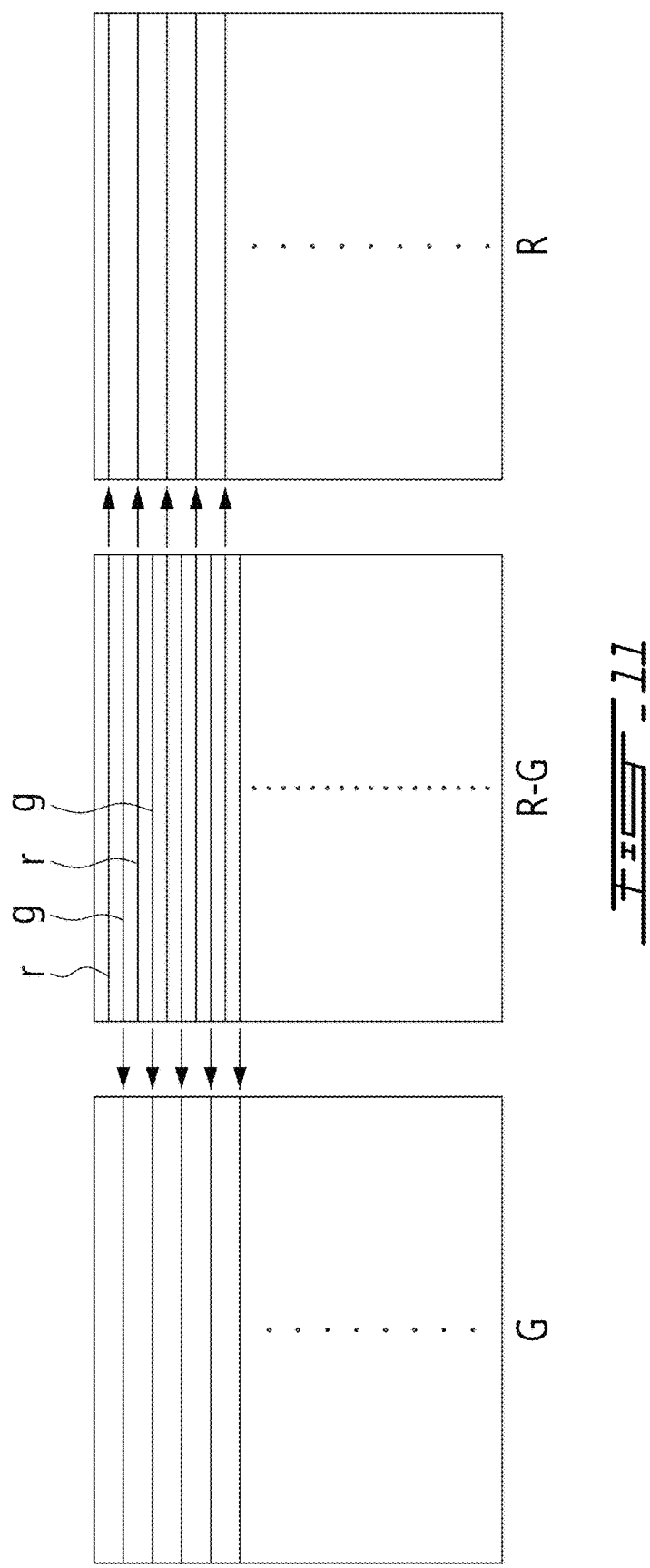
FIG. 11 is a schematic representation of a separating step applied to interlaced reflection intensity image data.

Referring now to FIG. 11, according to the dual laser embodiment, the interlaced sequences of image data is de-interlaced by image processing to provide two distinct image frames of substantially the same board surface, provided the raster pitch (i.e. the resulting spacing between the interlaced image lines) is sufficiently small, while providing acceptable image resolution. In the example shown, the image lines designated by "r" as obtained from a first, red wavelength laser, are extracted from the interlaced sequences of image data "R-G" to generate a first de-interlaced color image frame "R", and the image lines designated by "g" as obtained from a second, green wavelength laser, are extracted from the interlaced sequences of image data "R-G" to generate a second de-interlaced color image frame "G". For example, with a typical board feeding speed of 2500 mm/s, an activation frequency of 2500 Hz or more can be used to provide a maximum raster pitch of 1 mm in the interlaced image data, from which two de-interlaced color image frames of 2 mm or better resolution can be generated.

Turning again to FIGS. 6 and 7, according to an example of image data processing according to the invention, the computer 69 is programmed to process the color image frames (or sequences of de-interlaced color image frames) forming the target image data generated by camera 51 of imaging sensor unit 22, by applying a correction calculated from a comparison between the reflection intensity image data associated with the target surface 56 as generated by the first imaging sensor unit 22, and reflection intensity image data associated with the reference surface 56', as generated by the second imaging sensor unit 22' having its optical components substantially not subjected to the adverse external condition. The computer 69 is further programmed to apply the correction data to the reflection intensity image data associated with the target surface to generate corrected intensity image data compensating for the adverse external condition.

In one embodiment, the calculation of correction data involves image pixels corresponding to at least one reflection-based characteristic common to both target and reference surfaces 56, 56' and present over a major part thereof. According to that embodiment, the image pixels corresponding to the common reflection-based characteristic are obtained by filtering the reflected intensity image data associated with the target and reference surfaces 56, 56' to remove image pixels corresponding to reflection-based characteristics not common to these surfaces. For so doing, both of the target image data and reference image data are first analyzed to detect various reflection-based characteristics. Then, image pixels corresponding to selected reflection-based characteristics that are specific (i.e. not common) to any of the target or reference surface 56, 56' are removed therefrom by filtering, keeping image pixels corresponding to the common reflection-based characteristics. For example, in the context of optical surface inspection of wooden boards produced from a given wood species such as maple, the pixels corresponding to reflection-related characteristics of the scanned surface associated with detected knots, mineral streaks, slits and heartwood are removed from the image data, while pixels corresponding to a reflection-related characteristic associated with sapwood (high luminance) are kept, which can be typically detected using an appropriate minimum light intensity threshold. In another example involving optical surface inspection of wooden boards produced from another wood species such as oak, the pixels corresponding to reflection-related characteristics of the scanned surface associated with detected knots, mineral streaks, slits and sapwood are removed from the image data, while pixels corresponding to a reflection-related characteristic associated with heartwood (low luminance) are kept, which can be typically detected using an appropriate maximum light intensity threshold.

Figure 12:
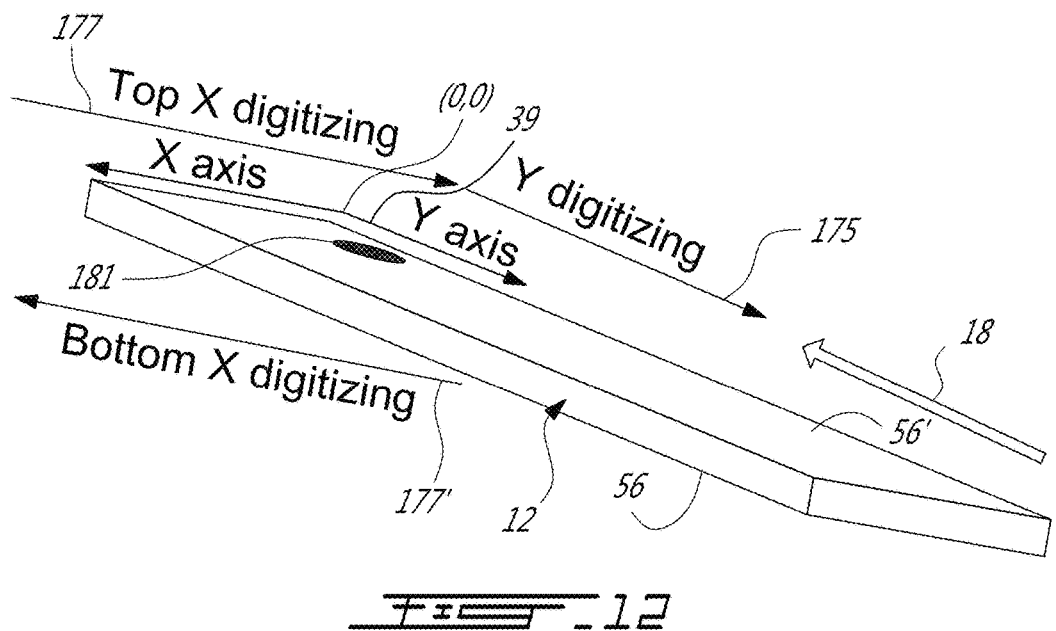
FIG. 12 is a schematic perspective view of a wooden board under scanning, showing the reference coordinates and directions for image digitizing.
Figure 12A:
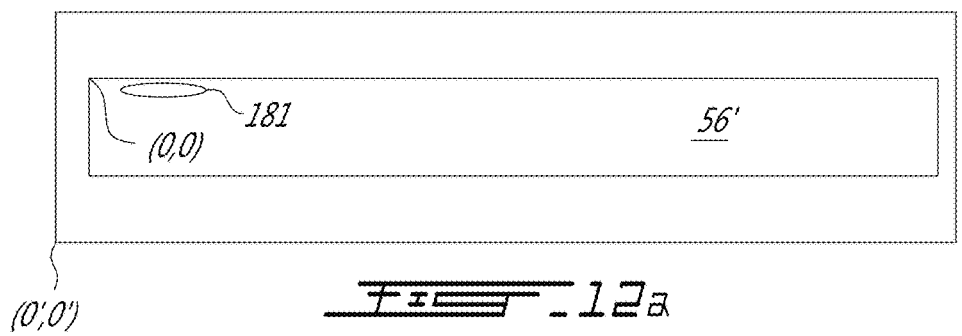
FIGS. 12a and 12b are raw image representations of top and bottom surfaces of the wooden board of FIG. 12.
Figure 12B:
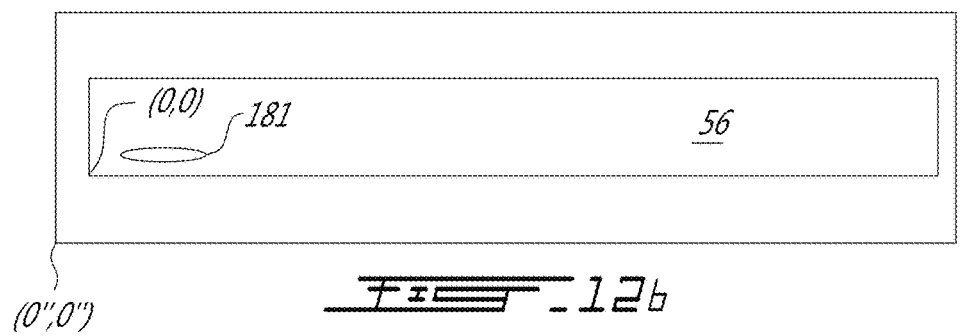

An example of a method whereby reflection intensity image data can be analyzed for purposes of characteristic detection and image correction will now be explained in detail in view of FIGS. 12 to 13. Referring to FIG. 12, a wooden board 12 to be inspected as transported through the scanning apparatus in the direction of arrow 18 is depicted with respect to a reference system 39 defining X and Y axis, whose origin coordinates (0, 0) correspond to board origin coordinates. The digitizing process along Y axis is performed by each imaging sensor unit in the direction of arrow 18 for both target (bottom) and reference (top) surfaces 56, 56' of board 12, while the digitizing process along X axis for the same target and reference surfaces 56, 56' is performed along directions of arrows 177 and 177', respectively. A linear digital camera provided with a CCD array being conveniently used, the scanned board is displaced perpendicularly with respect to the CCD array to form a two-dimensional image. While the resolution in the direction of the CCD array is intrinsic to pixel density thereof, the resolution along the perpendicular direction will be determined by the relative distance traversed by the board 12 between two successive image acquisition steps. For example, if the image acquisition rate is 1250 line/sec with a board moving at a speed of 55 m/min, a resolution between two consecutive acquired image lines of about 1 mm will be obtained. The raw image representations of board reference and target surfaces 56', 56 of FIG. 12 resulting from the digitizing process are respectively shown in FIGS. 12a and 12b, wherein it can be seen that origin coordinates (0, 0) of board reference surface 56' do not correspond to image origin coordinates (0',0') as shown at the bottom left corner. Similarly, it can be seen from FIG. 12b that origin coordinates (0,0) of board target surface 56 do not correspond to image origin coordinates (0",0") as shown at the bottom left corner. It can further be seen from FIG. 12 in view of FIGS. 12a and 12b that a defect such as hole 181 extending throughout board 12 appears at the upper left corner of the image representation of FIG. 12a, while it appears at the lower left corner of the image representation of FIG. 12b. In order to simplify image data analyzing and processing, the raw image representations are conveniently realigned with respect to the board origin coordinates (0, 0) as shown in FIGS. 12c and 12d, by translating the image origin coordinates (0, 0) of reference surface 56' and image origin coordinates (0", 0") of board target surface 56 to the lower left corner of the board representation. It can further be seen from FIG. 12d that such translation makes target surface image origin coordinates (0", 0") to coincide with board origin coordinates (0,0). The resulting aligned image data are then analyzed by the programmed computer to identify, locate and classify defects and other visual characteristics represented by polygon-defining data including cartesian coordinates in actual distance unit (usually in μm) with respect to the physical reference system used. An appropriate classifier can be readily developed by any person skilled in the art of computer programming, based on the teaching of known references such as Fukunaga "Introduction to statistical pattern recognition" Academic Press, 1990. An example of resulting analyzed image is given in FIG. 13, wherein an area presenting mineral streaks is delimited by a large, 6-side polygon 184 and an area containing a slit is delimited by a small rectangle at 186. It can be also seen from FIG. 13 that outer perimeter 188 of board 12 can similarly be approximated by a polygon that is itself delimited within large rectangle 190 having its upper left corner coinciding with origin coordinates (0, 0) of the reference system defining X and Y axes. Conveniently, each polygon-delimited area on board surface images can be displayed on the computer monitor using a color specific to the type of defect or other characteristics so detected. The computer is further programmed to store in memory detected characteristic data in the form of data files containing polygon-defining data with associated defect or other characteristic identification data, as well as corresponding dimensional data such as estimated width, length and surface area. Using these data files, image pixels corresponding to selected reflection-based characteristics that are specific (i.e. not common) to any of the target or reference surface 56, 56' are removed from the associated reflection intensity data by filtering, keeping image pixels corresponding to the common reflection-based characteristics.

Then, the correction may be calculated by the programmed computer from a comparison between the filtered reflection intensity image data associated with the target surface 56 as generated by the first imaging sensor unit 22, and filtered reflection intensity image data associated with the reference surface 56', as generated by the second imaging sensor unit 22' having its optical components substantially not subjected to the adverse external condition. In the embodiment based on filtered reflection intensity image data considering the reflection-based characteristic common to both object surfaces and generally found over a major part thereof, for purposes of correction calculation, it is assumed that if the target image data were not likely to be defective due to the averse external condition (e.g. soiling caused by dirt and dust) to which the optical components associated with the first imaging sensor unit are subjected, a comparison ratio of mean luminance measured for the filtered image data of the reference surface $\overline{L}_{FR}$ on mean luminance measured for the filtered image data of the target surface $\overline{L}_{FT}$ would be approximately equal to 1:

$$\frac{\overline{L}_{FR}}{\overline{L}_{FT}} \cong 1 \tag{1}$$

Based on the above assumption (1), in an actual case where the target reflection intensity data is likely to be defective due to soiling of the optical components associated with the image sensor unit used, the proposed correction can be obtained as follows:

$$C = \frac{\overline{L}_{FR}}{\overline{L}_{FT}} \geq 1 \tag{2}$$

wherein:
C represents the correction data;
$\overline{L}_{FR}$ represents a mean value of the filtered reflected intensity image data associated with the reference surface; and
$\overline{L}_{FT}$ represents a mean value of the filtered reflected intensity image data associated with the target surface.

Then, the corrected intensity image data compensating for the adverse external condition are generated using the following relation:

$$I_{TC} = C \cdot I_T \tag{3}$$

wherein:
$I_{TC}$ represents the corrected intensity image data associated with the target surface; and
$I_T$ represents the reflected intensity image data associated with the target surface.

The above approximate assumption (1) on which calculation of the correction is based, reflects that some variability of reflection-based characteristics can be still observed between the target and reference filtered image data even using an image sensor unit provided with clean optical components, which variability is inherent to the inspected objects when taken individually. Moreover, as explained above, the level of optical component soiling due to the adverse external condition varies with time. In order to compensate for such variability and to provide adaptation to varying soiling conditions, an embodiment of the proposed method involves a learning mode based on a moving average calculation, wherein the target and reference surfaces of a plurality of objects are scanned, the correction data being calculated by averaging over a moving window the filtered reflected intensity image data associated with the scanned target and reference surfaces. In an embodiment, the correction factor is calculated by averaging filtered image data of the reference surface $\overline{\overline{L}}_{FR}$ and filtered image data of the target surface $\overline{\overline{L}}_{FT}$ as obtained from a predetermined number of lastly scanned image lines. For example, the last 100 000 scanned image lines may be retained for averaging, which corresponds to a scanned length of 100 m along Y axis in a case where the image sensor resolution is 1 mm/pixel. An algorithm to calculate the corrected target image data from the target raw image data can be based on the following relations:

$$\overline{\overline{L}}_{FR} = \frac{\sum_{1}^{N} \overline{L}_{FR}}{N} \tag{4}$$

$$\overline{\overline{L}}_{FT} = \frac{\sum_{1}^{N} \overline{L}_{FT}}{N} \tag{5}$$

$$C_N = \frac{\overline{\overline{L}}_{FR}}{\overline{\overline{L}}_{FT}} \geq 1 \tag{6}$$

$$I_{TC} = C_N \cdot I_T \tag{7}$$

wherein:
$\overline{\overline{L}}_{FR}$ represents an average, over N scan image lines defining the moving window, obtained from mean values of filtered image data $\overline{L}_{FR}$ associated with the scanned reference surfaces;
$\overline{\overline{L}}_{FT}$ represents an average, over N scan image lines defining the moving window, obtained from mean values of filtered image data $\overline{L}_{FT}$ associated with the scanned target surfaces;
$C_N$ represents the correction data derived by averaging from N scan image lines of the filtered image data;
$I_{TC}$ represents the corrected intensity image data associated with the target surface; and
$I_T$ represents the reflected intensity image data associated with the target surface.

Figure 14:
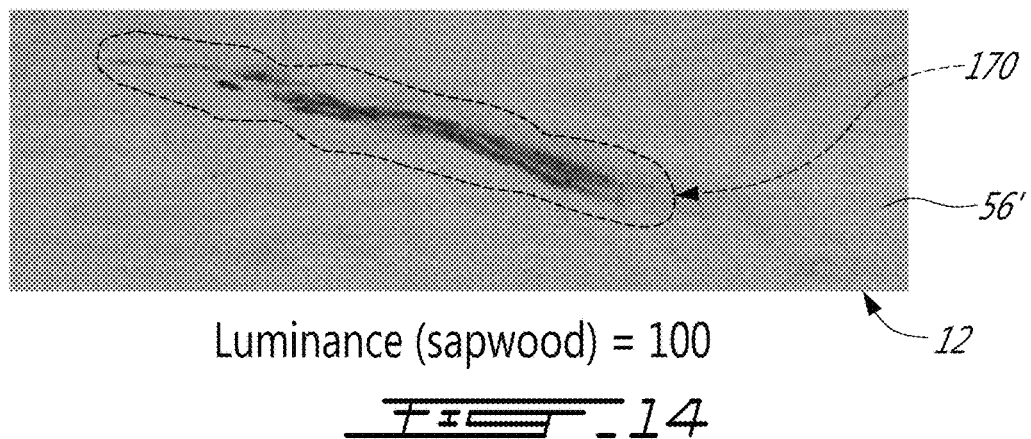
FIG. 14 is a raw image of a reference, top surface of a wooden board, showing a reflection-based characteristic specific to the board reference surface, corresponding the a local mineral streak.
Figure 15:
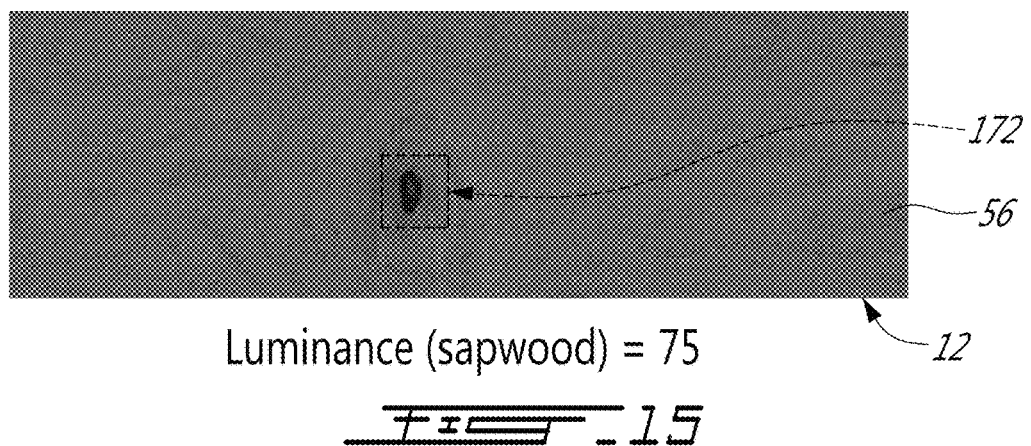
FIG. 15 is a raw image of a target, bottom surface of the same wooden board of FIG. 14, showing a reflection-based characteristic specific to the board reference surface, corresponding to a local wood knot.
Figure 16:
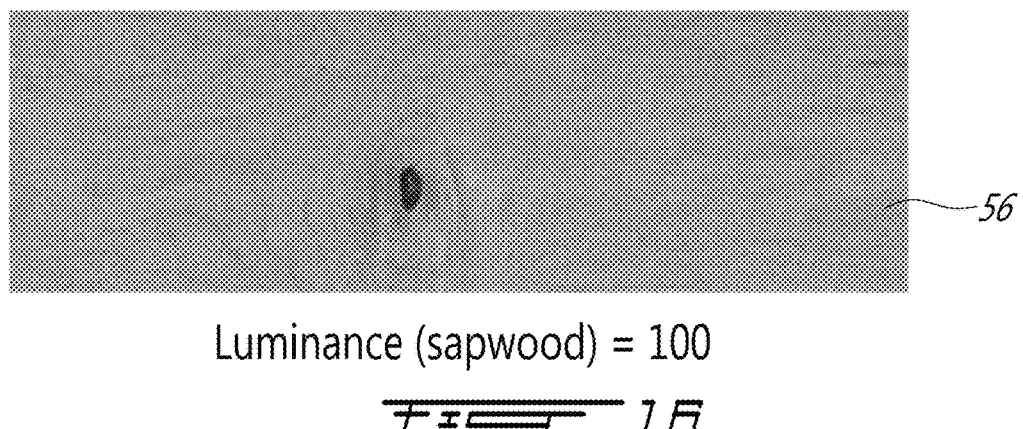
FIG. 16 is a corrected image corresponding to the raw image of the board target surface of FIG. 15, as obtained with the method in accordance to the present invention.

An example of image processing in accordance with the correction method described above will now be presented in view of FIGS. 14 to 16. In FIG. 14, there is represented a raw image of reference (top) surface 56' of a wooden board 12, showing a detected local mineral streak delimited by polygon 170 to be removed for purposes of calculating the required correction. A mean luminance $\overline{L}_{FR}$=100 associated with sapwood has been calculated from filtered image data of the reference surface. Referring to FIG. 15, from a raw image of target (bottom) surface 56 of the same wooden board, shown in transparency according to a realigned spatial reference systems as explained above in view of FIGS. 12c and 12d, a local knot delimited by polygon 172 is detected and then removed for purposes for purposes of calculating the required correction. A mean luminance $\overline{L}_{FT}$=75 associated with sapwood has been calculated from a filtered image data of the target surface. Then, a correction C=1.333 is obtained and applied to the raw image of the target (bottom) surface 56, to obtain a corrected image as shown in FIG. 16. The resulting mean luminance $\overline{L}_{FT}$=100 of the corrected image which is associated with sapwood is the same as that of filtered image data associated with reference surface 56' shown in FIG. 14, indicating that the correction has been performed adequately.

In the context of the dual laser embodiment described above with reference of FIG. 7 in view of FIG. 11, the corrected de-interlaced color image frames can be analyzed separately or in combination to detect desired board characteristics. In the latter case, the computer 69 may be further programmed to compare the complementary color image frames one with another to detect one or more characteristics of the board surface. For example, the comparison may consist of dividing one of the complementary color image frames by the other and comparing the division resulting image data with a predetermined threshold, which can allow improved detection capabilities over analysis of single color intensity data. As an illustration in a context of inspection of boards made of red oak, while the analysis of single color intensity data obtained through red wavelength laser illumination may reliably discriminate between dark and pale areas, such analysis may not distinguish sapwood areas, generally characterized by grey shade, from heartwood areas that are rather of red shade, since such sapwood and heartwood areas can seem both dark or pale on the basis of single color intensity data. However, by dividing one of the complementary color image frames by the other on a pixel by pixel basis, e.g. color image R/color image G, and comparing the division resulting image data with a predetermined threshold T', discrimination may be obtained considering that the mean intensity ratio R/G of grey shade characterizing a sapwood area on a board made of red oak wood is significantly lower to typical red shade area characterizing a heartwood area on the same board. In practice, the mean intensity ratio R/G of grey shade being near 1 (i.e. red intensity substantially equates green intensity), a threshold T'=1 may be used, so that a heartwood area is detected whenever R/G>1.

In an embodiment, assuming that the board is moving at known speed or position/time data along the travel path axis, the data processing means is further programmed for assembling the reflected laser intensity image data with corresponding data representing sensed location on the board surface, so that the detection of the characteristics may include data relating to identification and location thereof. In the case where profile-related image data are produced simultaneously to the interlaced sequences of reflected laser intensity image data, the assembling task is performed accordingly in a same manner. Optionally, in order to generate full color (RGB) image data, a third laser source generating light in the blue wavelength range may be added to obtain a third color image frame. Alternatively, a blue (B) image may be estimated from known reflectance characteristics of the board material at a typical blue wavelength, to allow generation of a color (RGB) image for displaying purposes.

The invention claimed is:

1. An apparatus for optically scanning a surface of an object under an external soiling condition, comprising:
   a first imaging sensor unit having one or more optical components subjected to said external soiling condition, a sensing field defining a scanning zone intersecting a target surface of the object, and being configured for generating reflection intensity image data associated with said target surface;
   a second imaging sensor unit having one or more optical components not subjected to said external soiling condition, a sensing field defining a scanning zone intersecting a reference surface of the object different from said target surface and being configured for generating reflection intensity image data associated with said reference surface;
   data processing means programmed to calculate correction data from a comparison between said reflected intensity image data associated with said target and reference surfaces, and further programmed to apply the correction data to the reflected intensity image data associated with said target surface to generate corrected intensity image data compensating for said external soiling condition.

2. The apparatus according to claim 1, wherein said correction data calculation involves image pixels corresponding to at least one reflection-based characteristic common to both said surfaces and present over a major part thereof.

3. The apparatus according to claim 2, wherein said image pixels corresponding to the common reflection-based characteristic are obtained by filtering said reflected intensity image data associated with said target and reference surfaces to remove image pixels corresponding to reflection-based characteristics not common to the target and reference surfaces.

4. The apparatus according to claim 3, wherein said correction data are calculated using the following relation:

$$C = \frac{\overline{L}_{FR}}{\overline{L}_{FT}} \geq 1$$

wherein:
   C represents said correction data;
   $\overline{L}_{FR}$ represents a mean value of the filtered reflected intensity image data associated with said reference surface; and
   $\overline{L}_{FT}$ represents a mean value of the filtered reflected intensity image data associated with said target surface.

5. The apparatus according to claim 4, wherein the corrected intensity image data compensating for said external soiling condition are generated using the following relation:

$$I_{TC} = C \cdot I_T$$

wherein:

$I_{TC}$ represents the corrected intensity image data associated with said target surface; and $I_T$ represents the reflected intensity image data associated with said target surface.

6. An apparatus for optically scanning a surface of at least one of a plurality of objects being serially transported under an external soiling condition, comprising:

a first imaging sensor unit having one or more optical components subjected to said external soiling condition, a sensing field defining a scanning zone intersecting a target surface of the object and being configured for generating reflection intensity image data associated with said target surface;

a second imaging sensor unit having one or more optical components not subjected to said external soiling condition, a sensing field defining a scanning zone intersecting a reference surface of the object different from said target surface and configured for generating reflection intensity image data associated with said reference surface;

data processing means programmed to calculate correction data from a comparison between said reflected intensity image data associated with said target and reference surfaces, and further programmed to apply the correction data to the reflected intensity image data associated with said target surface to generate corrected intensity image data compensating for said external soiling condition.

7. The apparatus according to claim 6, wherein said correction data calculation involves image pixels corresponding to at least one reflection-based characteristic common to both said surfaces and present over a major part thereof.

8. The apparatus according to claim 7, wherein said image pixels corresponding to said common reflection-based characteristic are obtained by filtering intensity image data associated with said target and reference surfaces to remove image pixels corresponding to reflection-based characteristics not common to the target and reference surfaces.

9. The apparatus according to claim 8, wherein the target and reference surfaces of more than one of said plurality of objects are scanned, said correction data being calculated by averaging over a moving window the filtered reflected intensity image data associated with the scanned target and reference surfaces.

10. The apparatus according to claim 9, wherein said correction data are calculated using the following relations:

$$\overline{L}_{FR} = \frac{\sum_{1}^{N} \overline{L}_{FR}}{N}$$

$$\overline{L}_{FT} = \frac{\sum_{1}^{N} \overline{L}_{FT}}{N}$$

$$C_N = \frac{\overline{L}_{FR}}{\overline{L}_{FT}} \geq 1$$

$$I_{TC} = C_N \cdot I_T$$

wherein:

$\overline{L}_{FR}$ represents an average, over N scan image lines defining said moving window, obtained from mean values of filtered image data $\overline{L}_{FR}$ associated with said scanned reference surfaces;

$\overline{L}_{FT}$ represents an average, over N scan image lines defining said moving window, obtained from mean values of filtered image data $\overline{L}_{FT}$ associated with said scanned target surfaces;

$C_N$ represents said correction data derived by averaging from N scan image lines of said filtered image data;

$I_{TC}$ represents the corrected intensity image data associated with said target surface; and $I_T$ represents the reflected intensity image data associated with said target surface.

11. A method for optically scanning a surface of an object under external soiling condition, for use with a first imaging sensor unit having one or more optical components subjected to said external soiling condition, a sensing field defining a scanning zone intersecting a target surface of the object and configured for generating reflection intensity image data associated with said target surface, comprising the steps of:

i) providing a second imaging sensor unit having one or more optical components not subjected to said external soiling condition, a sensing field defining a scanning zone intersecting a reference surface of the object different from said target surface, and being configured for generating reflection intensity image data associated with said reference surface;

ii) calculating correction data from a comparison between said reflected intensity image data associated with said target and reference surfaces; and iii) applying the correction data to the reflected intensity image data associated with said target surface to generate corrected intensity image data compensating for said external soiling condition.

12. The method according to claim 11, wherein said correction data calculation involves image pixels corresponding to at least one reflection-based characteristic common to both said surfaces and generally found over a major part thereof.

13. The method according to claim 12, wherein said image pixels corresponding to common reflection-based characteristic are obtained by filtering said reflected intensity image data associated with said target and reference surfaces to remove image pixels corresponding to reflection-based characteristics not common to the target and reference surfaces.

14. The method according to claim 13, wherein said correction data are calculated using the following relation:

$$C = \frac{\overline{L}_{FR}}{\overline{L}_{FT}} \geq 1$$

wherein:

C represents said correction data;

$\overline{L}_{FR}$ represents a mean value of the filtered reflected intensity image data associated with said reference surface; and $\overline{L}_{FT}$ represents a mean value of the filtered reflected intensity image data associated with said target surface.

15. The method according to claim 14, wherein the corrected intensity image data compensating for said external soiling condition are generated using the following relation:

$$I_{TC} = C \cdot I_T$$

wherein:
- $I_{TC}$ represents the corrected intensity image data associated with said target surface; and
- $I_T$ represents the reflected intensity image data associated with said target surface.

16. A method for optically scanning a surface of at least one of a plurality of objects being serially transported under external soiling condition, for use with a first imaging sensor unit having one or more optical components subjected to said external soiling condition, a sensing field defining a scanning zone intersecting a target surface, and being configured for generating reflection intensity image data associated with said target surface, comprising the steps of:
   i) providing a second imaging sensor unit having one or more optical components not subjected to said external soiling condition, a sensing field defining a scanning zone intersecting a reference surface of the object different from said target surface, and being configured for generating reflection intensity image data associated with said reference surface;
   ii) calculating correction data from a comparison between said reflected intensity image data associated with said target and reference surfaces; and
   iii) applying the correction data to the reflected intensity image data associated with said target surface to generate corrected intensity image data compensating for said external soiling condition.

17. The method according to claim 16, wherein said correction data calculation involves image pixels corresponding to at least one reflection-based characteristic common to both said surfaces and present over a major part thereof.

18. The method according to claim 17, wherein said image pixels corresponding to said common reflection-based characteristic are obtained by filtering intensity image data associated with said target and reference surfaces to remove image pixels corresponding to reflection-based characteristics not common to the target and reference surfaces.

19. The method according to claim 18, wherein the target and reference surfaces of more than one of said plurality of objects are scanned, said correction data being calculated by averaging over a moving window the filtered reflected intensity image data associated with the target and reference scanned surfaces.

20. The method according to claim 19, wherein said correction data are calculated using the following relations:

$$\overline{L}_{FR} = \frac{\sum_{1}^{N} \overline{L}_{FR}}{N}$$

$$\overline{L}_{FT} = \frac{\sum_{1}^{N} \overline{L}_{FT}}{N}$$

$$C_N = \frac{\overline{L}_{FR}}{\overline{L}_{FT}} \geq 1$$

$$I_{TC} = C_N \cdot I_T$$

wherein:
- $\overline{L}_{FR}$ represents an average, over N scanned lines defining said moving window, obtained from mean values of filtered image data $\overline{L}_{FR}$ associated with said scanned reference surfaces;
- $\overline{L}_{FT}$ represents an average, over N scanned lines defining said moving window, obtained from mean values of filtered image data $\overline{L}_{FT}$ associated with said scanned target surfaces;
- $C_N$ represents said correction data derived by averaging from N scanned lines of said filtered image data;
- $I_{TC}$ represents the corrected intensity image data associated with said target surface; and
- $I_T$ represents the reflected intensity image data associated with said target surface.

21. The method according to claim 20, wherein said object is made of wood, said characteristics which are not common to the target and reference surfaces are selected from the group consisting of knots, slits, mineral streaks, sapwood and heartwood.

* * * * *